US008506953B2

(12) United States Patent
Böttner et al.

(10) Patent No.: US 8,506,953 B2
(45) Date of Patent: Aug. 13, 2013

(54) USE AND METHODS FOR PREVENTING AND/OR TREATING ORAL MALODOUR

(75) Inventors: Mewes Böttner, Berlin (DE); Christine Lang, Berlin (DE); Markus Veen, Altmühldorf (DE); Michael Schilling, Berlin (DE); Andreas Reindl, Moscow (RU)

(73) Assignee: BASF SE, Lugwigshafen (DE)

( * ) Notice: Subject to any disclaimer, the term of this patent is extended or adjusted under 35 U.S.C. 154(b) by 57 days.

(21) Appl. No.: 12/997,035

(22) PCT Filed: May 19, 2009

(86) PCT No.: PCT/EP2009/003586
§ 371 (c)(1),
(2), (4) Date: Dec. 9, 2010

(87) PCT Pub. No.: WO2009/149816
PCT Pub. Date: Dec. 17, 2009

(65) Prior Publication Data
US 2011/0097284 A1    Apr. 28, 2011

(30) Foreign Application Priority Data

Jun. 11, 2008   (EP) .................................... 08010641

(51) Int. Cl.
*A01N 63/00*    (2006.01)
(52) U.S. Cl.
USPC ..................................................... 424/93.45
(58) Field of Classification Search
None
See application file for complete search history.

(56) References Cited

U.S. PATENT DOCUMENTS

| 3,957,974 | A | 5/1976 | Hata |
| 4,746,512 | A | 5/1988 | Kawai et al. |
| 7,052,688 | B2 | 5/2006 | De Simone |
| 2002/0168388 | A1 | 11/2002 | Borchert et al. |
| 2004/0101495 | A1 | 5/2004 | Nase et al. |
| 2005/0019894 | A1 | 1/2005 | Park |
| 2008/0247993 | A1 | 10/2008 | Reindl et al. |

FOREIGN PATENT DOCUMENTS

| DE | 10101294 A1 | 7/2002 |
| EP | 1312667 A1 | 5/2003 |
| EP | 1634948 A1 | 3/2006 |
| GB | 1584694 | 2/1981 |
| WO | WO-00/78322 A2 | 12/2000 |
| WO | WO-03/055987 A1 | 7/2003 |
| WO | WO-2004/067729 A1 | 8/2004 |
| WO | WO-2006/022471 A1 | 3/2006 |
| WO | WO-2006/027265 A1 | 3/2006 |

OTHER PUBLICATIONS

Chung, et al., "Isolation and characterization of *Lactobacillus* species inhibiting the formation of *Streptococcus* mutans biofilm", Oral Microbiology Immunology, 2004, vol. 19, No. 3, pp. 214-216.
Krueger, C., et al., "In situ delivery of passive immunity by *Lactobacilli* producing single-chain antibodies", Nature Biotechnology, vol. 20, Jul. 2002, pp. 702-706.
Loesche, W. J., "Role of *Streptococcus* mutans in Human Dental Decay", Microbiological Reviews, Dec. 1986, pp. 353-380.
Sookkhee, S., et al., "Lactic acid bacteria from healthy oral cavity of Thai volunteers: inhibition of oral pathogens", Journal of Applied Microbiology, 2001, vol. 90, No. 2, pp. 172-179.
Wei H., et al., "Stability and activity of specific antibodies against *Streptococcus* mutans and *Streptococcus sorbinus* in bovine milk fermented with *Lactobacillus rhamnosus* strain GG or treated at ultra-high temperature", Oral Microbiology Immunology, 2002, vol. 17, No. 1, pp. 9-15.
Whatmore, A. M., et al. "Re-evaluation of the texonomic position of *Streptococcus ferus*", International Journal of Ssystematic and Evolutionary Microbiology, 2002, vol. 52, No. 5, pp. 1783-1787.
Song et al, FEMS Microbiology Letters, "Rapid identification of 11 human intestinal *Lactobacillus*. . .", vol. 187, No. 2, Jun. 15, 2000, pp. 167-173, XP002225666, ISSN:0378-1097.
Schleifer et al, Systemic and Applied Microbiology, "Phylogeny of the genus *Lactobacillus* and related genera", vol. 18, No. 4, 1995, pp. 461-467, XP009074893, ISSN:0723-2020.
Benthin, S., et al., "Amino Acid Utilization by *Lactococcus lactis* subsp. *cremoris* FD1 During Growth on Yeast Extract or Casein Peptone", Journal of Applied Bacteriology, vol. 80, (1996), pp. 65-72.
Burton, J.P., et al., "A Preliminary Study of the Effect of Probiotic *Streptococcus salivarius* K12 on Oral Malodour Parameters", Journal of Applied Microbiology, vol. 100, (2006), pp. 754-764.
Doran, A., et al., "Ecological Control: In Vitro Inhibition of Anaerobic Bacteria by Oral *Streptococci*", Microbial Ecology in Health and Disease, Taylor & Francis Health Sciencees, (2004), pp. 23-27.
Gaudreau, H., et al., "Effect of Ultrafiltration of Yeast Extracts on Their Ability to Promote Lactic Acid Bacteria Growth", Can. J. Microbiol., vol. 45, (1999), pp. 891-897.
Gaudreau, H., et al., "The Use of Crude Cellular Extracts of *Lactobacillus delbrueckii* ssp. *bulgaricus* 11842 to Stimulate Growth of a Probiotic *Lactobacillus rhamnosus* Culture in Milk", Enzyme and Microbial Technology, vol. 36, (2005), pp. 83-90.
Hojo, K., et al., "Reduction of Vitamin K Concentration by Salivary Bifidobacterium Strains and Their Possible Nutritional Competition with *Porphyromonas gingivalis*", Journal of Applied Microbiology, vol. 103, (2007), pp. 1969-1974.

(Continued)

*Primary Examiner* — Brian J Gangle
(74) *Attorney, Agent, or Firm* — Novak Druce Connolly Bove + Quigg LLP

(57) ABSTRACT

Described is a microorganism belonging to the group of lactic acid bacteria which is able to drastically reduce the peptide concentration in saliva thereby depleting the substrate used by anaerobic microorganisms of the oral micro-flora which are the causative agent for oral malodour. Moreover, described is a microorganism belonging to the group of lactic acid bacteria which is able to stimulate the growth of *Streptococcus salivarius* but does not stimulate the growth of *Streptococcus mutans* and/or *Porphyromonas gingivalis*. Also described are compositions containing the above-mentioned microorganisms, their use for preventing and/or treating oral malodour and/or halitosis and to methods for preventing and/or treating oral malodour and/or halitosis.

20 Claims, 7 Drawing Sheets

(56) References Cited

OTHER PUBLICATIONS

Kim, J-D., et al., "Isolation of *Lactobacillus sakei* Strain KJ-2008 and Its Removal of Characteristic Malodorous Gases Under Anaerobic Culture Conditions", Biosci. Biotechnol. Biochem., vol. 68, No. 12, (2004), pp. 2427-2435.

Kim, J-D., et al., "Isolation and Identification of a Lactic Acid Bacterial Strain KJ-108 and Its Capability for Deodorizing Malodorous Gases Under Anaerobic Culture Conditions", J. Microbiol. Biotechnol., vol. 13, No. 2, (2003), pp. 207-216.

Takahashi N., et al., "Dipeptide Utilization by the Periodontal Pathogens *Porphyromonas gingivalis. Prevotella intermedia, Prevotella nigrescens* and *Fusobacterium necleatum*", Oral Microbiology Immunology, vol. 17, (2002), pp. 50-54.

Tang-Larsen, J., et al., "Competition for Peptides and Amino Acids Among Periodontal Bacteria", Journal of Periodontal Research, vol. 30, (1995), pp. 390-395.

Wåler, S.M., "On the Transformation of Sulfur-Containing Amino Acids and Peptides to volatile Sulfur Compounds (VSC) in the Human Mouth", Eur J. Oral Sci., vol. 105, (1997), pp. 534-537.

USE AND METHODS FOR PREVENTING AND/OR TREATING ORAL MALODOUR

RELATED APPLICATIONS

This application is a national stage application under 35 U.S.C. §371 of PCT/EP2009/003586, filed May 19, 2009, which claims benefit of European application 08010641.2, filed Jun. 11, 2008.

The present invention relates to a microorganism belonging to the group of lactic acid bacteria which is able to drastically reduce the peptide concentration in saliva thereby depleting the substrate used by anaerobic microorganisms of the oral microflora which are the causative agent for oral malodour. Moreover, the present invention relates to a microorganism belonging to the group of lactic acid bacteria which is able to stimulate the growth of *Streptococcus salivarius* but does not stimulate the growth of *Streptococcus mutans* and/or *Porphyromonas gingivalis*.

The present invention also relates to compositions containing the above-mentioned microorganisms, their use for preventing and/or treating oral malodour and/or halitosis and to methods for preventing and/or treating oral malodour and/or halitosis.

A common problem in oral hygiene is chronic bad breath (halitosis). The prevalent method to treat halitosis is to mask or neutralise the offensive odour by the use of mouthwashes or chewing-gums that contain e.g. menthol. However, these methods only are effective in the short-term, but not in the long-term. Therefore, a need exists for long-term methods to prevent or treat halitosis. This problem has been addressed in the state of the art by different methods which more or less all aim at reducing the number of anaerobic bacteria that produce "volatile sulphur compounds" (VSCs) such as hydrogen sulphide and methyl mercaptan, for example.

One described method for reducing these bacteria is to remove tongue coating with a tongue scraper in order to eliminate substrates for bacterial proliferation from the tongue. Another method is to treat the tongue with a metal salt such as zinc chloride or a disinfectant such as alcohol or chlorhexidine. However, the disadvantage of these methods is that the metal salt and disinfectant inhibit the growth of other harmless or even beneficial oral microorganisms as well.

One approach to treat or prevent halitosis which has been described is to maintain the pH of saliva at a physiologically normal level. It is known that microbial species associated with caries and mucosal infections favour an acidic pH; microbial species associated with the development of periodontal disease favour a pH above normal, whereas microbial species associated with good oral health favour a neutral pH. Compositions containing probiotic bacteria (e.g. *Lactobacillus* and *Streptococcus*) that use this mechanism are disclosed in US200707137 and US2006018843. WO2007/077210 discloses a method for re-establishment of an oral micro-flora associated with good oral health that uses weak or non-acid producing probiotics chosen from a group of early colonizing oral bacteria that are normally present in a healthy oral microflora (e.g. *Streptococcus (oralis), Eubacterium, Neisseria, Veillonea*) in combination with substances having pH-rising or pH-buffering substances (e.g. bicarbonates, carbamides, phosphates, proteins and/or salts). US2006045870 discloses live lactic acid bacteria belonging to the genus *Weisella* that inhibit the growth of VSC-producing bacteria by interacting with them and generating hydrogen peroxide under aerobic and anaerobic conditions. US2006171901 discloses another method of inhibiting growth of anaerobic bacteria, particularly halitosis causing bacteria, which involves BLIS (bacteriocin-like inhibitory substances)-producing *Streptococcus salivarius* strains and extracts thereof.

A disadvantage of the methods that are available for the prevention and the treatment of halitosis is that most of these methods not only inhibit the growth of the VSC-producing bacteria that are known as the major cause of oral malodour, but they inhibit the growth of other harmless oral microorganisms as well.

The object of the present invention is therefore to provide alternative means and methods for the prevention and/or the treatment of oral malodour and/or halitosis.

Accordingly, in a first aspect the present invention relates to a microorganism belonging to the group of lactic acid bacteria characterized in that it shows the following property (b) when subjected to the following assay (a):

Assay (a):

(a) the microorganism is cultivated for 24 h at 37° C. under anaerobic conditions in a synthetic medium containing 15 g/l peptides with a starting cell density of $1 \times 10^7$ cells/ml;

(b) the cells are removed by centrifugation at 4000×g for 15 min; and (c) the peptide concentration in the resulting supernatant is determined;

Property (b):

The microorganism leads to a reduction of the peptide concentration in the culture medium so that the peptide concentration in the supernatant after the incubation for 24 h is reduced by at least 20% in comparison to the starting concentration of 15 g/l, i.e. the microorganism is capable of reducing the peptide concentration in the medium in the assay (a) by at least 20%.

In a preferred embodiment the microorganism according to the invention furthermore shows the following property (B), when subjected to the following assay (A):

(a) the microorganism is cultured in 100 ml synthetic medium at 37° C. for 24 h under anaerobic conditions with a starting cell density of $1 \times 10^7$ cells/ml;

(b) subsequently the cells are centrifuged at 4000×g for 15 min and resuspended in 20 ml $H_2O$;

(c) subsequently the cells are frozen to −80° C. and lyophilized under vacuum for 16 h;

(d) 10 mg of the lyophilized bacteria are resuspended in $H_2O$ and centrifuged at 4000×g for 10 min;

(e) 1 ml of synthetic medium containing 7 g/l peptides is added to the cell pellet, the cells are resuspended in the medium and after 5 min of aerobic incubation at 37° C. the cells are removed by centrifugation at 4000×g for 15 min; and (f) the peptide concentration in the resulting medium supernatant is determined;

Property (B): the lyophilized bacteria lead to a reduction of the peptide concentration in the resulting medium supernatant by at least 20% in comparison to the concentration of the medium at the beginning of the incubation period (7 g/l).

In a preferred embodiment the peptide concentration in assay (a) or (A) is reduced by the microorganism according to the invention by at least 30%, more preferably by at least 40% and even more preferably by at least 50%.

In a particularly preferred embodiment the microorganism according to the invention is capable of reducing the peptide concentration in Assay (A) by at least 60% even more preferably by at least 70%.

The present invention thus provides a microorganism which can effectively reduce the peptide concentration in its environment, in particular also in saliva, as is described in the appended Examples. As is known, oral malodour is caused by the fact that the ratio between the healthy oral mouth flora (constituted mostly by *Streptococcus salivarius*) and the pathogenic oral mouth flora (constituted mostly by anaerobic gram-negative bacteria) is shifted to the anaerobic gram-negative bacteria which decompose proteins present in saliva to volatile compounds. This leads to the production of volatile sulphur compounds which cause the oral malodour.

The microorganism of the present invention is capable of reducing oral malodour by reducing the amount of peptides and thereby depleting the substrate of the anaerobic gram-negative of the oral flora.

The term "synthetic medium" refers to a chemically defined medium, i.e. a medium of which the chemical composition is known. The synthetic medium can be any synthetic medium suitable for the cultivation of the microorganism in question. In one preferred embodiment the synthetic medium is a synthetic medium as disclosed in U.S. Pat. No. 6,340,585.

In a preferred embodiment the synthetic medium is a medium with the following composition:

| | |
|---|---|
| Guanine: | 0.1 g/l |
| Cytosine: | 0.1 g/l |
| Thymidine: | 0.1 g/l |
| 2'-Deoxyadenosine: | 0.1 g/l |
| 2'-Deoxyuridine: | 0.1 g/l |
| $K_2HPO_4$: | 2 g/l |
| Sodium-Acetate: | 5 g/l |
| $MgSO_4$-Heptahydrate: | 0.1 g/l |
| di-Ammonium hydrogen citrate: | 2 g/l |
| $CaCl_2$-dihydrate: | 0.5 g/l |
| Oleic Acid: | 0.1% (w/v) |
| Cyanocobalamine: | 0.02 mg/l |
| Riboflavine: | 10 mg/l |
| Folic Acid: | 0.2 mg/l |
| Pyridoxal-5-phosphate-monohydrate: | 10 mg/l |
| 4-Aminobenzoic acid: | 0.2 mg/l |
| D (+)-Biotin: | 1 mg/l |
| Ascorbic Acid: | 500 mg/l |
| Nicotinic Acid: | 10 mg/l |
| Ca-Panthotenate: | 10 mg/l |
| Thiamine: | 1 mg/l |
| Cobalt(II)-Nitrat-Hexahydrate: | 500 mg/l |
| $MnSO_4$-Monohydrate: | 20 mg/l |
| $MgSO_4$-Heptahydrate: | 500 mg/l |
| $Na_2MoO_4$: | 0.04 mg/l |
| PTU-Extract (Ohly, Deutsche Hefewerke Germany): | 15 g/l (or as stated elsewhere) |
| D-Glucose-Monohydrate: | 10 g/l |

The term "containing 15 g/l peptides" (or "containing 7 g/l peptides") means that the synthetic medium at the beginning of the incubation period contains 15 g/l peptides (or 7 g/l peptides, respectively). In principle the peptides may be any kind of peptides. In a preferred embodiment the peptides contained in the synthetic medium are in the form of a yeast extract, preferably PTU extract. PTU extract can be purchased from Ohly, Deutsche Hefewerke, Germany. It is an ultrafiltrated low salt yeast extract with a high content of easy available peptides and preferably shows the following characteristics:

Average Analysis:

| | |
|---|---|
| Dry matter: | 96% |
| Protein (N × 6,25) in d.m.: | 72.9% |
| Total nitrogen in d.m.: | 11.7% |
| NaCl: | ≦1.0% |
| Ash: | 10% |
| pH (in 2% solution): | 5.7 |

Vitamins (Typical):

| | |
|---|---|
| Thiaminhydrochlorid × HCl (B1): | 1.2 mg/100 g |
| Riboflavin (B2): | 7.0 mg/100 g |
| Pyridoxin × HCl (B6): | 5.9 mg/100 g |
| Nicotinic acid: | 47.8 mg/100 g |
| Biotin: | 0.022 mg/100 g |
| Ca-D-Pantothenate: | 17.9 mg/100 g |
| Folic acid: | 3.7 mg/100 g |

Amino acid profile (typical): as shown in FIG. 7

The term "a starting cell density of cells/all" means that the synthetic medium is inoculated at the beginning of the cultivation period with the microorganism so that $1 \times 10^7$ cells/ml are present in the medium.

The peptide concentration can be determined by any method known to the person skilled in the art. Well established methods are, e.g., the methods according to Biuret, Lowry or Bradford. Moreover, any commercially available kit or other tool for determining the peptide concentration can be employed. One preferred example are tools or kits based on fluorescence dye such as the Quant-it Protein kit of Invitrogen. The reduction in peptide concentration in the above mentioned assays (a) and/or (A) is preferably assayed as described in the appended Examples.

As shown in the appended Examples, it has surprisingly been found that lactic acid bacteria can be identified which have the capability to drastically reduce in their environment the peptide concentration. This effect is not only observed with live bacteria but also with lyophilized forms. Moreover, it is shown in the Examples that the microorganisms according to the invention show the above mentioned effect not only in the above described assays but also in saliva and that the presence of the microorganism according to the invention leads to a remarkable reduction in the production of $H_2S$ when added to saliva.

In particular, in a preferred embodiment the microorganism according to the invention also show the following property (d) when subjected to the following assay (c):

Assay (c):
(a) the microorganism is cultured in 100 ml synthetic medium at 37° C. for 24 h under anaerobic conditions with a starting cell density of $1 \times 10^7$ cells/ml;
(b) subsequently the cells are centrifuged at 4000×g for 15 min and resuspended in 20 ml $H_2O$;
(c) subsequently the cells are frozen to −80° C. and lyophilized under vacuum for 16 h;
(d) 10 mg of the lyophilized bacteria are resuspended in $H_2O$ in a deep-well plate and centrifuged at 4000×g for 10 min;
(e) 1 ml of synthetic medium containing 3 g/l peptides are added to the pellet and after 5 min of incubation at 37° C. the cells are removed by centrifugation at 4000×g for 15min;
(f) the supernatant is then transferred to a new deep-well plate and subsequently inoculated with 10 to 100 μl, preferably 50 μl unsterile human saliva and anaerobically incubated for 6 h at 37° C., while the deep-well plate is covered with a sterile filter paper impregnated with lead acetate;
(g) the production of hydrogen sulphide by the microorganisms in the reaction is monitored by determining the blackening of the filter paper;

Property (d): In the presence of the microorganism according to the invention the blackening of the lead acetate impregnated filter paper is reduced in comparison to a control in which the medium was not preincubated with said microorganism. The reduced blackening of the filter paper is indicative of a reduced production of $H_2S$ by the bacteria contained in the unsterile human saliva used to inoculate the medium.

The term "a reduced production of $H_2S$" means a reduction in $H_2S$ production of at least 10%, more preferably of at least 20% even more preferably of at least 30% and particularly preferred of at least 40% or even of at least 50% in comparison to the control. The reduction can be measured, e.g., by densiometrically analyzing the blackening of the filter paper. Alternatively, the production of hydrogen sulphide in steps (f) and (g) is not measured by the use of a filter paper but is measured by a Headspace analysis using gas chromatography.

The present invention in a second aspect also relates to a microorganism belonging to the group of lactic acid bacteria characterized in that it is capable of stimulating the growth of *Streptococcus salivarius* but does not stimulate the growth of *Streptococcus mutans* and/or *Porphyromonas gingivalis*.

The term "stimulates" in connection with the growth of microorganisms of the species *Streptococcus salivarius* means that the growth of this microorganisms is increased when contacted with a microorganism according to the invention. An increased growth means preferably an increase in proliferation, i.e. cell divisions per time unit. Alternatively, the term "stimulates" also refers to an increase in size of individual cells. Bacterial cell size can be assessed by flow cytometry (e.g. Becton-Dickinson FACSort flow cytometer, San Jose, Calif.) after staining with the stain SYBR Green I (Molecular Probes, USA). Bacteria cell size is assessed in Side-Angle Light Scatter (SSC) mode. An increased growth thus means an increase in biomass production per time unit.

The stimulation of growth of the respective microorganism can preferably be observed in vitro, more preferably in an assay in which a microorganism according to the invention is contacted with *Streptococcus salivarius* and the growth of *Streptococcus salivarius* is determined. The growth can be determined by counting the numbers of cells/colonies after different time intervals of incubation and can be compared with a control which does not contain a microorganism according to the invention, thereby allowing to determine whether there is an increase in growth.

An in vitro assay for determining the stimulation of growth is described in the Examples and comprises a so-called "Photometric co-incubation-assay". In brief, such an assay comprises the following steps:

(a) the microorganism belonging to the group of lactic acid bacteria to be tested is mixed with *Streptococcus salivarius* in a cell count ratio of 1:100 (lactic acid bacterium: *Streptococcus salivarius*) in ½ TSY medium;
(b) the culture suspension is aerobically incubated for 12 h at 37° C.;
(c) as a control unconsumed ½ TSY medium or MRS light medium is used;
(d) the maximum optical density ($OD_{600, max}$) is determined and/or the maximum growth rate ($V_{max}$) is determined during exponential growth; and
(e) the microorganism is classified as a microorganism capable of stimulating the growth of *Streptococcus salivarius*, if the maximum optical density ($OD_{500, max}$) and/or the maximum growth rate ($V_{max}$) is increased by at least 10% in comparison to the control.

The term "½ TSY medium" refers to TSY medium which is diluted in a ratio of 1:1 (vol:vol) with $H_2O$.

In a preferred embodiment the incubation is carried out in a 96-well-plate. In a further preferred embodiment the incubation is carried out in a Bio Tek PowerWave microplate spectrophotometer (Biotek Instruments GmbH, Germany).

Preferably the $OD_{600, max}$ and the $V_{max}$ are determined as follows:

The optical density at an OD of 600 is measured for an extended period of time, preferably about 8 to 12 h, after the start of the incubation, at regular intervals, e.g. every 2.5 minutes. For the determination of $OD_{600, max}$ the determination of the $OD_{600}$ is preferably carried out for 10 h after incubation.

For the determination of $OD_{600, max}$ the mean value is calculated from the three highest measured values.

$V_{max}$ is preferably determined by selecting 15 consecutive values which show the steepest gradient. The unit for indicating $V_{max}$ is mOD/min. The determination of the $OD_{600}$ for the calculation of $V_{max}$ is preferably carried out over a period of time which allows to cover the exponential growth phase of the cultured microorganism.

Preferably the microorganism according to the present invention leads to an increase of the maximum optical density ($OD_{600, max}$) or the maximum growth rate ($V_{max}$) of *Streptococcus salivarius* in the above-described assay of at least 15%, more preferably of at least 20%, even more preferably of at least 30% and particularly preferred of at least 40%, 50%, 60%, 70% or even 80% in comparison to the control.

In a preferred embodiment the above described microorganism according to the invention does not only stimulate the growth of *Streptococcus salivarius* but also stimulates the growth of at least one further microorganism of the healthy oral micro-flora. Examples for such microorganisms are *Streptococcus oralis* and *Streptococcus epidermidis*. The stimulation of these bacteria can be measured by the assay as described above.

The above described microorganism according to the invention is also characterized in that it does not stimulate the growth of *Streptococcus mutans* and/or of *Porphyromonas gingivalis*. A microorganism is regarded as not stimulating the growth of a microorganism of the transient pathogenic micro flora if it does not lead to an increased growth of *Streptococcus mutans* and/or of *Porphyromonas gingivalis* when contacted with it. The stimulation of growth or its absence can be tested in vitro. An in vitro assay for determining the stimulation of growth or its absence is described in the Examples and comprises a so-called "Photometric co-incubation-assay". In brief, such an assay in the case of *Streptococcus mutans* comprises the following steps:

(a) the microorganism belonging to the group of lactic acid bacteria to be tested is cultured under anaerobic conditions in 96-well-plates with 150 µl of synthetic medium for 24 h at 37° C., the cells are pelleted by centrifugation at 4000×g for 15 min and the supernatant is recovered;
(b) *Streptococcus mutans* is cultured anaerobically in 5 ml TSY medium in closed 15-ml Falcon tubes overnight at 37° C.;
(c) the *Streptococcus mutans* cell culture is mixed in a volumetric ratio of 2:1 with the supernatant of step (a);
(d) the culture suspension is incubated aerobically for 12 h at 37° C.;
(e) as a control unconsumed ½ TSY medium or MRS light medium is used;
(f) the maximum optical density ($OD_{600, max}$) is determined and/or the maximum growth rate ($V_{max}$) is determined during exponential growth; and
(g) the microorganism is classified as a microorganism which is not capable of stimulating the growth of *Streptococcus mutans* if the maximum optical density ($OD_{600, max}$) and/or the maximum growth rate ($V_{max}$) is not increased in comparison to the control.

Alternatively, such an assay may comprise the following steps:
(A) the microorganism belonging to the group of lactic acid bacteria to be tested is mixed with *Streptococcus salivarius* in a cell count ratio of 1:100 (*lactobacillus:S. mutans*) in ½ TSY medium;
(B) the culture suspension is aerobically incubated for 12 h at 37° C.;
(C) as a control unconsumed ½ TSY medium or MRS light medium is used;
(D) the maximum optical density ($OD_{600,max}$) is determined and/or the maximum growth rate ($V_{max}$) is determined during exponential growth; and
(E) the microorganism is classified as a microorganism which is not capable of stimulating the growth of *Streptococcus mutans* if the maximum optical density ($OD_{600,max}$) and/or the maximum growth rate ($V_{max}$) is not increased in comparison to the control.

In the case of *Porphyromonas gingivalis* the assay comprises the following steps:
(h) the microorganism belonging to the group of lactic acid bacteria to be tested is cultured under anaerobic conditions in 96-well-plates with 150 µl of synthetic medium for 24 h at 37° C., the cells are pelleted by centrifugation at 4000×g for 15 min and the supernatant is recovered;
(i) *Porphyromonas gingivalis* is cultured anaerobically in 5 ml FAB medium in closed 15-ml Falcon tubes overnight at 37° C.;
(j) the *Porphyromonas gingivalis* cell culture is mixed in a volumetric ratio of 2:1 with the supernatant of step (h);
(k) the culture suspension is incubated anaerobically for 45 h at 37° C.;
(i) as a control unconsumed FAB medium is used;
(m) the optical density ($OD_{600}$) is determined after 10, 15, 21, 39 and 45 h of incubation ($OD_{600}$); and
(n) the microorganism is classified as a microorganism which is not capable of stimulating the growth of *Porphyromonas gingivalis* if the optical density ($OD_{600}$) at each time of measuring is not increased in comparison to the control.

Alternatively, such an assay comprises the following steps:
(H) the microorganism belonging to the group of lactic acid bacteria to be tested is mixed with *Porphyromonas gingivalis* in a cell count ratio of 1:100 (*lactobacillus:P. gingivalis*) in FAB medium;
(I) the culture suspension is aerobically incubated for 45 h at 37° C.;
(J) as a control unconsumed FAB medium is used;
(K) the maximum optical density ($OD_{600,max}$) is determined and/or the maximum growth rate ($V_{max}$) is determined during exponential growth; and
(L) the microorganism is classified as a microorganism which is not capable of stimulating the growth of *Porphyromonas gingivalis* if the maximum optical density ($OD_{600,max}$) and/or the maximum growth rate ($V_{max}$) is not increased in comparison to the control.

In a preferred embodiment the incubation in steps (d) and (B) are carried out in a 96-well-plate. In a further preferred embodiment the incubation is carried out in a Bio Tek PowerWave microplate (Fa. Biotek Instruments GmbH, Germany) spectrophotometer.

In a preferred embodiment the incubation in steps (k) and (I) are carried out in a 96-well-plate. In a further preferred embodiment the incubation is carried out in a Whitley DG250 anaerobic workstation (Meintrup-DWS, Germany).

With respect to $OD_{600,max}$ and $V_{max}$ the same applies as has been set forth herein further above.

A microorganism is regarded as not stimulating the growth of a microorganism of *Streptococcus mutans* or *Porphyromonas gingivalis* if the growth is not increased or only slightly increased when contacted with the former microorganism. "Slightly increased" means that the growth is increased not more than by 5% when compared to the control, more preferably not more than 2% when compared to the control. The term "not increased" means that there can be found no statistically relevant difference between the growth of *Streptococcus mutans* or *Porphyromonas gingivalis* when contacted with a microorganism of the invention when compared to the control where no microorganism of the invention is present. The term "not increased" in a preferred embodiment also includes those cases where a microorganism actually leads to a decrease of the growth of *Streptococcus mutans* or *Porphyromonas gingivalis*, i.e. where it represses the growth of such a microorganism.

In another preferred embodiment the microorganism of the present invention does not negatively influence the growth of *Streptococcus mutans* or *Porphyromonas gingivalis*. The term "not negatively influence" means that there can be found no inhibition of the growth of the *Streptococcus mutans* or *Porphyromonas gingivalis* when contacted with a microorganism of the invention when compared to the control where no microorganism of the invention is present.

In a preferred embodiment the microorganism according to the invention does not only not stimulate the growth of *Streptococcus mutans* and/or *Porphyromonas gingivalis* but also does not stimulate the growth of at least one further pathogenic microorganism of the oral micro-flora. Representatives of pathogenic oral bacteria are anaerobic, gram-negative bacteria. Further examples are *Actinobacillus actinomycetemcomitans, Actinomyces naeslundii, Fusobacterium nucleatum, Fusobacterium nucleatum polymorphum, Prevotella intermedia, Solobacterium moorei, Streptococcus gordonii, Streptococcus mitis, Streptococcus sanguinis, Tannerella forsynthensis* and *Treponema denticola*.

The stimulation or absence of stimulation of growth of these bacteria can be measured by the assays as described above for *S. mutans* and *P. gingivalis*.

In a preferred embodiment the above described microorganisms according to the invention are characterized in that they not only show the effect of stimulating the growth of *Streptococcus salivarius* as living cells but also as culture supernatant. This means that also a culture supernatant obtained from a microorganism according to the invention shows the effect of stimulating the growth of *Streptococcus salivarius*. Preferably this effect occurs in the following assay:
(a) *Streptococcus salivarius* is cultured anaerobically in 6-well-plates with 8 ml TSY medium over night at 37° C.;
(b) the microorganism belonging to the group of lactic acid bacteria to be tested is cultured under anaerobic conditions in 96-well-plates with 150 µl of synthetic medium for 24 h at 37° C., the cells are pelleted by centrifugation at 4000×g for 15 min and the supernatant is recovered;
(c) the *Streptococcus salivarius* cell culture of step (a) is mixed in a volumetric ratio of 2:1 to 4:1 with the supernatant of step (b) in ½ TSY medium;
(d) the culture suspension is incubated aerobically for 12 h at 37° C.;
(e) as a control unconsumed % TSY or MRS light medium is used;
(f) the maximum optical density ($OD_{600, max}$) is determined and/or the maximum growth rate ($V_{max}$) is determined during exponential growth; and (g) the microorganism is classified as a microorganism capable of stimulating the growth of *Streptococcus salivarius* if the maximum optical density ($OD_{600, max}$) and/or the maximum growth rate ($V_{max}$) is increased by at least 10% in comparison to the control.

In a preferred embodiment the incubation is carried out in a 96-well-plate. In a further preferred embodiment the incubation is carried out in a Bio Tek PowerWave microplate spectrophotometer (Biotek Instruments GmbH, Germany).

With respect to $OD_{600, max}$ and $V_{max}$ the same applies as has been set forth herein further above.

Preferably the microorganism according to the present invention leads to an increase of the maximum optical density ($OD_{600, max}$) or the maximum growth rate ($V_{max}$) of *Streptococcus salivarius* in the above-described assay of at least 15%, more preferably of at least 20%, even more preferably of at least 30% and particularly preferred of at least 40%, 50%, 60%, 70% or even 80% in comparison to the control.

In a particularly preferred embodiment the stimulation of growth of *Streptococcus salivarius* shown by the microorganism according to the invention is resistant to heat treatment, i.e. it also occurs when the cells (or extracts thereof) or the culture supernatant is subjected to a heat treatment. The heat treatment is preferably a heat treatment at a temperature of between 60° C. and 100° C., more preferably of between 70° C. and 90° C., even more preferably between 75° C. and 85° C. and most preferably at a temperature of around 80° C. or exactly 80° C.

Generally, the heat treatment should last for a period of time of at least 1 minute. Preferably, the heat treatment lasts for a period of time of at least n minutes, wherein n is an integer in the range of 2 to 60, with n=10 or 15 or 20 being particularly preferred. However, there is in principle no upper limit for the time of incubation. However, it is preferably no longer than 4, 3, 2 or 1 hour(s). The most preferred heat treatment is for about 10 minutes at a temperature of 80° C. in an incubator. The most preferred heat treatment is considered as abolishing any function of a protein and of any vitality of cells, which thus distinguishes the above mentioned microorganism belonging to the group of lactic acid bacteria from other microorganism in that it is still capable of stimulating the growth of *Streptococcus salivarius*. Hence, it is very useful for use in any food, feed, drink or composition in the context of the present invention if it is desired that the microorganism should not be alive. well-plate. After cooling down, the capability of the microorganism according to the invention (or extracts thereof) or of the culture supernatant thereof to stimulate the growth of *Streptococcus salivarius* is determined in an assay as described herein above or as described in the appended Examples. In the context with the culture supernatant of a microorganism according to the invention a corresponding assay preferably comprises the following steps:

(h) *Streptococcus salivarius* is cultured anaerobically in 6-well-plates with 8 ml TSY medium over night at 37° C.;

(i) the microorganism belonging to the group of lactic acid bacteria to be tested is cultured under anaerobic conditions in 96-well-plates with 150 μl of synthetic medium for 24 h at 37° C., the cells are pelleted by centrifugation at 4000×g for 15 min and the supernatant is recovered;

(j) the supernatant is incubated at 80° C. for 10 min in an incubator and is subsequently cooled to room temperature;

(k) the *Streptococcus salivarius* cell culture of step (a) is mixed in a volumetric ratio of 2:1 with the supernatant of step (j) in ½ TSY medium;

(l) the culture suspension is incubated aerobically for 12 h at 37° C.;

(m) as a control unconsumed ½ TSY or MRS light medium is used;

(n) the maximum optical density ($OD_{600, max}$) is determined and/or the maximum growth rate ($V_{max}$) is determined during exponential growth; and (o) the microorganism is classified as a microorganism capable of stimulating the growth of *Streptococcus salivarius* if the maximum optical density ($OD_{600, max}$) and/or the maximum growth rate ($V_{max}$) is increased by at least 10% in comparison to the control.

Moreover, also the property of non-stimulation of the growth of *Streptococcus mutans* and/or of *Porphyromonas gingivalis* of the microorganism according to the invention is resistant to heat treatment. With respect to the definition of the term heat treatment the same applies as has been set forth above.

In another preferred embodiment the stimulation of growth of *Streptococcus salivarius* shown by the microorganism according to the invention is resistant to lyophilisation, i.e. it also occurs when the cells are subjected to a lyophilisation treatment. The lyophilisation treatment is preferably a lyophilisation treatment in which the cells (or extracts thereof) or the cell supernatant are first frozen to −80° C. and are subsequently lyophilized under vacuum for 16 h. After the lyophilisation treatment the capability of the microorganism according to the invention to stimulate the growth of *Streptococcus salivarius* can be tested by the assays already described above or as described in the appended Examples. In the context with the culture supernatant of a microorganism according to the invention a corresponding assay preferably comprises the following steps:

(p) *Streptococcus salivarius* is cultured anaerobically in 6-well-plates with 8 ml TSY medium over night at 37° C.;

(q) the microorganism belonging to the group of lactic acid bacteria to be tested is cultured under anaerobic conditions in 50 ml of synthetic medium in closed 100 ml bottles overnight at 37° C., the cells are pelleted by centrifugation at 4000×g for 15 min and the supernatant is recovered;

(r) 20 ml of the supernatant of step (q) is frozen to −80° C. and lyophilized under vacuum for 16 h;

(s) The lyophilized supernatant is resuspended in 20 ml $H_2O$;

(t) the *Streptococcus salivarius* cell culture of step (a) is mixed in a volumetric ratio of 2:1 with the supernatant of step (s) in ½ TSY medium in 96 well plates;

(u) the culture suspension is incubated aerobically for 12 h at 37° C.;

(v) as a control unconsumed ½ TSY or MRS light medium is used;

(w) the maximum optical density ($OD_{600, max}$) is determined and/or the maximum growth rate ($V_{max}$) is determined or during exponential growth; and (x) the microorganism is classified as a microorganism capable of stimulating the growth of *Streptococcus salivarius* if the maximum optical density ($OD_{600, max}$) and/or the maximum growth rate ($V_{max}$) is increased by at least 10% in comparison to the control.

According to a particularly preferred embodiment the microorganism according to the invention shows both the properties described in the first and second aspect of the invention, respectively, i.e. it shows the properties (b) and/or (B) as described in the first aspect (drastic reduction in peptide concentration) and it shows the properties as described in the second aspect (stimulating the growth of *Streptococcus salivarius* and not stimulating the growth of *Streptococcus mutans* and/or *Porphyromonas gingivalis*).

The microorganisms according to the invention as described herein above, due to their properties, allow to shift the balance of the oral micro-flora towards *Streptococcus salivarius* which leads to an improvement as regards the development of less malodour.

As is evident from the above, all the above-mentioned characteristics render the above mentioned microorganism belonging to the group of lactic acid bacteria a suitable agent for reducing oral malodour and/or halitosis or for preventing and/or treating oral malodour and/or halitosis, in particular oral malodour and/or halitosis which is caused by pathogenic microorganisms of the oral microbial flora, in particular anaerobic, gram-negative bacteria. Accordingly, the microorganism according to the invention has an effect on the reduction of oral malodour and is thus a useful agent for preventing and/or treating oral malodour and/or halitosis.

The term "preventing oral malodour" includes prophylaxis of oral malodour. Accordingly, a subject who has never been encountered with those microorganisms, which are responsible for the development of oral malodour, but may be at a risk of being encountered, i.e. infected with such microorganisms, or a subject which still has a well-balanced oral microflora benefits, for example, from the microorganisms, compositions, uses and methods of the present invention insofar as said subject will not suffer from oral malodour. Hence, the microorganisms, compositions, uses and methods of the present invention may, for example, be applied to infants, children or young animals for prophylaxis of oral malodour since the infant's or young animal's oral cavity is normally free of microorganisms responsible for the development of oral malodour. However, the microorganisms and compositions as used in accordance with the present invention are not limited to administration to infants, children or young animals.

The terms "treating oral malodour" and "treating halitosis" include administration of the microorganisms or compositions as described herein to a subject suffering from oral malodour and/or halitosis for the purpose of diminishing the amount of malodour produced.

Optionally, the microorganism according to the present invention is a probiotic microorganism which has, besides its oral malodour reducing effect, beneficial effects to the host organism to which it is administered. A "probiotic", by the generally accepted definition, is a "live microbial feed supplement which beneficially affects the host animal by improving its intestinal microbial balance".

Accordingly, the present invention provides the use of easily administrable bacteria, which are food-grade organisms that may, in addition to their effect of reducing oral malodour, be useful as probiotics.

Strikingly, the effect of the microorganisms according to the invention of efficiently removing peptides from a medium and, thus, also from saliva thereby preventing other microorganism present in the oral microflora which are responsible for the production of substances leading to the generation of oral malodour to produce the corresponding substances, can also be observed with inactivated forms of the microorganisms, such as lyophilized forms or forms resulting from a treatment with UV light or radiation.

Most importantly, the effect also occurs in the presence of saliva which renders the microorganism according to the invention in particular suitable for the use in the form of oral applications or as an additive for food, feed or drinks. Remarkably, thermally inactivated or lyophilised forms, in particular analogs, derivatives or (a) fragment(s) of said microorganisms disclosed herein are still capable of specifically efficiently reducing the peptide concentration in the above described assays.

Similarly, also the property of the microorganism according to the present invention as described in the second aspect of the present invention, i.e. to stimulate the growth of *Streptococcus salivarius* and not to stimulate the growth of *Streptococcus mutans* and/or *Porphyromonas gingivalis*, occurs not only with the microorganisms themselves but also with the culture supernatant of the microorganism and with inactivated forms. In particular, the property of stimulating the growth of *Streptococcus salivarius* and not to stimulate the growth of *Streptococcus mutans* and/or *Porphyromonas gingivalis* is resistant to heat treatment and is resistant to a lyophilisation treatment.

These surprising effects are advantageous for using said inactivated forms, culture supernatants, analog(s) or fragment(s) of said microorganisms as well as mutants or derivatives thereof in compositions for use in animals, preferably, humans or mammals, to prevent and/or treat oral malodour and/or halitosis. In particular said inactivated forms, culture supernatants, analogs or fragments can be easily added to any composition, e.g. cosmetic or pharmaceutical composition, food or feedstuff or drinks and the like. Additionally, the production of such inactivated forms, culture supernatants, analogs or fragments is cheap and easy and they can be stored for prolonged periods of time without loosing their capability to reduce the peptide concentration and/or to stimulate the growth of *Streptococcus salivarius* and not to stimulate the growth of *Streptococcus mutans* and/or *Porphyromonas gingivalis*. A particular advantage of the microorganism according to the invention is that it retains its capability to reduce the peptide concentration and/or to stimulate the growth of *Streptococcus salivarius* and not to stimulate the growth of *Streptococcus mutans* and/or *Porphyromonas gingivalis* if it is lyophilised or spray-dried or dried. Moreover, the property to stimulate the growth of *Streptococcus salivarius* and not to stimulate the growth of *Streptococcus mutans* and/or *Porphyromonas gingivalis* is even retained after a heat treatment. The above mentioned properties make the microorganism according to the invention a favorable ingredient for use in the compositions described herein.

In addition, in a preferred embodiment, the microorganism according to the present invention shows the above described properties (i.e. reduction of concentration of peptides and/or stimulation of growth of *Streptococcus mutans* and non-stimulation of growth of *Streptococcus mutans* and/or *Porphyromonas gingivalis*) also in the presence of saliva. Saliva is an exogenous secrete which is synthesized by the salivary glands. It is a complex liquid containing, apart from about 99% water a multiplicity of organic and inorganic compounds. Physiological ingredients of saliva are, inter alia, enzymes, e.g., amylases, carboanhydrases, lysozyme, peroxidases or proteins, e.g., mucins, lactoferrin, proline-rich proteins, cystatines, histatines or statherines or soluble IgA. Thus, although a variety of potentially interfering substances are present in saliva, the above mentioned properties of the microorganism according to the invention are not hampered by the presence of saliva.

The aforementioned characteristics of the above mentioned microorganism belonging to the group of lactic acid bacteria renders it to be a robust and effective agent for preventing and/or treating oral malodour and/or halitosis since it is mainly administered in various forms to the mouth including the oral cavity and teeth where, inter alia, saliva including certain proteases and low pH values after ingestion of carbohydrate containing food stuff is present. Moreover, the resistance to heat and/or lyophilisation has beneficial effects in adding the above mentioned microorganism belonging to the group of lactic acid bacteria as additive to food stuff during the preparation of said food stuff. Namely, food stuff is often heat sterilized, pre-cooked, pasteurized and the like which is detrimental for viability of microorganisms.

Other embodiments and advantages of the invention are set forth in part in the description herein, and in part, may be obvious from the description, or may be learned from the practice of the invention.

Before the present invention is described in detail, it is to be understood that this invention is not limited to the particular methodology, protocols, bacteria, vectors, and reagents etc. described herein as these may vary. It is also to be understood that the terminology used herein is for the purpose of describing particular embodiments only, and is not intended to limit the scope of the present invention, which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölb. H. eds. (1995), Helvetica Chimica Acta, CH-4010 Basel, Switzerland). Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

It must be noted that as used herein and in the appended claims, the singular forms "a", "an", and "the", include plural referents unless the context clearly indicates otherwise. Thus, for example, reference to "a reagent" includes one or more of such different reagents, and reference to "the method" includes reference to equivalent steps and methods known to those of ordinary skill in the art that could be modified or substituted for the methods described herein.

When used in the context of the present invention, the term "microorganism belonging to the group of lactic acid bacteria" encompasses (a) microorganism(s) which belong(s) to bacteria, in particular belonging to gram-positive fermentative eubacteria, more particularly belonging to the family of lactobacteriaceae including lactic acid bacteria. In addition, said term also encompasses derivatives or mutants or analogs or fragments, such as a cell extracts or membrane fractions as described herein, of said microorganims(s), which retain the above described properties (i.e. reducing the concentration of peptides and/or to stimulate the growth of *Streptococcus mutans* and not to stimulate the growth of *Streptococcus mutans* and/or *Porphyromonas gingivalis*). The terms "derivative", "mutants", "analogs" and "fragments" are described elsewhere herein. Lactic acid bacteria are from a taxonomical point of view divided up into the subdivisions of *Streptococcus, Enterococcus, Leuconostoc*, and *Lactobacillus*. The above mentioned microorganism belonging to the group of lactic acid bacteria is preferably a *Lactobacillus* species. Members of the lactic acid bacteria group normally lack porphyrins and cytochromes, do not carry out electron-transport phosphorylation and hence obtain energy only by substrate-level phosphorylation. I.e. in lactic acid bacteria ATP is synthesized through fermentation of carbohydrates. All of the lactic acid bacteria grow anaerobically, however, unlike many anaerobes, most lactic acid bacteria are not sensitive to oxygen and can thus grow in its presence as well as in its absence. Accordingly, the above mentioned microorganisms belonging to the group of lactic acid bacteria are preferably aerotolerant anaerobic lactic acid bacteria, preferably belonging to the genus of *Lactobacillus*.

The above mentioned lactic acid bacteria are preferably rod-shaped or spherical, varying from long and slender to short bent rods, are moreover preferably immotile and/or asporogenous and produce lactic acid as a major or sole product of fermentative metabolism. The genus *Lactobacillus* to which the above mentioned microorganism belongs is divided up by the following characteristics into three major subgroups, whereby it is envisaged that the above mentioned *Lactobacillus* species can belong to each of the three major subgroups:

(a) homofermentative lactobacilli
   (i) producing lactic acid, preferably the L-, D- or DL-isomer(s) of lactic acid in an amount of at least 85% from glucose via the Embden-Meyerhof pathway;
   (ii) growing at a temperature of 45° C., but not at a temperature of 15° C.;
   (iii) being long-rod shaped; and
   (iv) having glycerol teichoic acid in the cell wall;
(b) homofermantative lactobacilli
   (i) producing lactic acid, preferably the L- or DL-isomer(s) of lactic acid via the Embden-Meyerhof pathway;
   (ii) growing at a temperature of 15° C., showing variable growth at a temperature of 45° C.;
   (iii) being short-rod shaped or coryneform; and
   (iv) having ribitol and/or glycerol teichoic acid in their cell wall;
(c) heterofermentative lactobacilli
   (i) producing lactic acid, preferably the DL-isomer of lactic acid in an amount of at least 50% from glucose via the pentose-phosphate pathway;
   (ii) producing carbondioxide and ethanol
   (iii) showing variable growth at a temperature of 15° C. or 45° C.;
   (iv) being long or short rod shaped; and
   (v) having glycerol teichoic acid in their cell wall.

Based on the above-described characteristics, the above mentioned microorganisms can be classified to belong to the group of lactic acid bacteria, particularly to the genus of *Lactobacillus*. By using classical systematics, for example, by reference to the pertinent descriptions in "Bergey's Manual of Systematic Bacteriology" (Williams & Wilkins Co., 1984), a microorganism can be determined to belong to the genus of *Lactobacillus*. Alternatively, the microorganisms can be classified to belong to the genus of *Lactobacillus* by methods known in the art, for example, by their metabolic fingerprint, i.e. a comparable overview of the capability of such (a) microorganism(s) to metabolize sugars or by other methods described, for example, in Schleifer et al., System. Appl. Microb., 18 (1995), 461-467 or Ludwig et al., System. Appl. Microb., 15 (1992), 487-501. The above mentioned microorganisms are capable of metabolizing sugar sources, which are typical and known in the art for microorganisms belonging to the genus of *Lactobacillus*. Preferably, however, the above mentioned microorganism has a metabolic fingerprint selected from the group consisting of:
(i) it metabolizes D-lactose, but not L-sorbose and/or D-saccharose and/or D-inuline,
(ii) it metabolizes inuline, (iii) it metabolizes L-sorbose, but not D-lactose and/or D-saccharose and/or inuline, and (iv) it metabolizes L-sorbose, D-lactose and inuline.

Preferably, the above mentioned microorganism has a metabolic fingerprint selected from the group consisting of:

(i) it metabolizes D-lactose, but not L-sorbose, D-saccharose and inuline, (ii) it metabolizes L-sorbose, D-lactose and inuline, but not D-saccharose, (iii) it metabolizes L-sorbose, but not D-lactose, D-saccharose and inuline, and (iv) it metabolizes L-sorbose, D-lactose, D-saccharose, but not inuline.

Of course, the above mentioned microorganism is not limited to the metabolization of the sugars mentioned in the aforementioned metabolic fingerprint pattern, but may be capable of metabolizing further sugars which are commonly metabolized by Lactobacillus species.

The affiliation of the above mentioned microorganisms to the genus of Lactobacillus can also be characterized by using other methods known in the art, for example, using SDS-PAGE gel electrophoresis of total protein of the species to be determined and comparing them to known and already characterized strains of the genus Lactobacillus. The techniques for preparing a total protein profile as described above, as well as the numerical analysis of such profiles, are well known to a person skilled in the art. However, the results are only reliable insofar as each stage of the process is sufficiently standardized. Faced with the requirement of accuracy when determining the attachment of a microorganism to the genus of Lactobacillus, standardized procedures are regularly made available to the public by their authors such as that of Pot et al., as presented during a "workshop" organized by the European Union, at the University of Ghent, in Belgium, on Sep. 12 to 16, 1994 (Fingerprinting techniques for classification and identification of bacteria, SDS-PAGE of whole cell protein). The software used in the technique for analyzing the SDS-PAGE electrophoresis gel is of crucial importance since the degree of correlation between the species depends on the parameters and algorithms used by this software. Without going into the theoretical details, quantitative comparison of bands measured by a densitometer and normalized by a computer is preferably made with the Pearson correlation coefficient. The similarity matrix thus obtained may be organized with the aid of the UPGMA (unweighted pair group method using average linkage) algorithm that not only makes it possible to group together the most similar profiles, but also to construct dendograms (see Kersters, Numerical methods in the classification and identification of bacteria by electrophoresis, in Computer-assisted Bacterial Systematics, 337-368, M. Goodfellow. A. G. O'Donnell Ed., John Wiley and Sons Ltd, 1985).

Alternatively, the affiliation of said microorganisms to the genus of Lactobacillus can be characterized with regard to ribosomal RNA in a so-called Riboprinter®. More preferably, the affiliation of the above mentioned species to the genus Lactobacillus is demonstrated by comparing the nucleotide sequence of the 16S ribosomal RNA of said bacteria, or of their genomic DNA which codes for the 16S ribosomal RNA, with those of other genera and species of lactic acid bacteria known to date. Another preferred alternative for determining the attachment of species to the genus Lactobacillus is the use of species-specific PCR primers that target the 16S-23S rRNA spacer region. Another preferred alternative is RAPD-PCR (Niqatu et al. in Antonie van Leenwenhoek (79), 1-6, 2001) by virtue of that a strain specific DNA pattern is generated which allows to determine the affiliation of an identified microorganisms to the genus of Lactobacillus. Further techniques useful for determining the affiliation of a microorganism to the genus of Lactobacillus are restriction fragment length polymorphism (RFLP) (Giraffa et al., Int. J. Food Microbiol. 82 (2003), 163-172), fingerprinting of the repetitive elements (Gevers et al., FEMS Microbiol. Lett. 205 (2001) 31-36) or analysis of the fatty acid methyl ester (FAME) pattern of bacterial cells (Heyrman et al., FEMS Microbiol. Lett. 181 (1991), 55-62). Alternatively, lactobacilli can be determined by lectin typing (Annuk et al., J. Med. Microbiol. 50 (2001), 1069-1074) or by analysis of their cell wall proteins (Gatti et al., Lett. Appl. Microbiol. 25 (1997), 345-348.

The above mentioned microorganisms are preferably lactic acid bacteria belonging to the genus of Lactobacillus, more preferably Lactobacillus species as described herein, in particular Lactobacillus bacteria belonging to a species selected from the group consisting of acidophilus, fermentum, lactis, delbrueckii, algidus, brevis, buchneri, casei, camelliae, coleohominis, crustorum, diolivorans, heterohiochii, hilgardii, kimchii, lindneri, oris, pantheris, parabuchner and saerimneri. Even more preferably said Lactobacillus is Lactobacillus acidophilus. However, the Lactobacillus species are not limited thereto. The above mentioned microorganisms may preferably be "isolated" or "purified". The term "isolated" means that the material is removed from its original environment, e.g. the natural environment if it is naturally occurring. For example, a naturally-occurring microorganism, preferably a Lactobacillus species, separated from some or all of the coexisting materials in the natural system, is isolated. Such a microorganism could be part of a composition, and is to be regarded as still being isolated in that the composition is not part of its natural environment. The term "purified" does not require absolute purity; rather, it is intended as a relative definition. Individual microorganisms obtained from a library have been conventionally purified to microbiological homogeneity, i.e. they grow as single colonies when streaked out on agar plates by methods known in the art. Preferably, the agar plates that are used for this purpose are selective for Lactobacillus species. Such selective agar plates are known in the art.

More preferably, the above mentioned microorganism belonging to the group of lactic acid bacteria is selected from the group consisting of Lactobacillus acidophilus having DSMZ accession number DSM 19825, DSM 19826, DSM 19827 or a mutant or derivative thereof, wherein said mutant or derivative retains the capability to reduce the peptide concentration in the assay (a) and/or (A) as described hereinabove. The term "Lactobacillus acidophilus having DSMZ accession number" relates to cells of a microorganism belonging to the species Lactobacillus acidophilus deposited by BASF AG with the Deutsche Sammlung für Mikroorganismen and Zellkulturen GmbH ("DSMZ") on Nov. 1, 2007 and having the following deposit numbers DSM 19825, DSM 19826, DSM 19827. The DSMZ is located at the Inhoffenstr. 7b, 38124 Braunschweig, Germany.

The aforementioned DSMZ deposits were made pursuant to the terms of the Budapest treaty on the international recognition of the deposit of microorganisms for purposes of patent procedure.

"A mutant or derivative" of the above mentioned microorganism belonging to the group of lactic acid bacteria, preferably of the deposited Lactobacillus acidophilus has preferably the same characteristics as the respective deposited strains, i.e. it retains the capability to reduce the peptide concentration in the assay (a) and or (A) as described hereinabove and/or it retains the capability to stimulate the growth of *Streptococcus mutants* and not to stimulate the growth of *Streptococcus mutans* and/or *Porphyromonas gingivalis*. For example, said derivative can be genetically engineered. In the context of the present invention the term "genetically engineered" is used in its broadest sense for methods known to the person skilled in the art to modify desired nucleic acids in vitro and in vivo such that genetic modifications are affected and genes are altered by recombinant DNA technology. Accordingly, it is preferred that said methods comprise cloning, sequencing and transformation of recombinant nucleic acids. For this purpose appropriate vectors including expression vectors for *Lactobacillus* species as, for example, described in EP-B1 506 789, EP-B1 316 677, EP-B1 251 064, EP-B1 218 230, EP-B1 133 046 or WO 89/01970.

Primers, enzymes, further host cells for cloning of intermediate constructs and the like can be used and are known by the skilled artisan. Preferably, genetically engineered mutants comprise cells of the above mentioned microorganism belonging to the group of lactic acid bacteria, preferably of the deposited *Lactobacillus* species harbouring recombinant nucleic acids either comprised in their bacterial chromosome or on (a) plasmid(s) or comprised in their bacterial chromosome and/or (a) plasmid(s). Said recombinant nucleic acids are preferably foreign to the above mentioned microorganism belonging to the group of lactic acid bacteria. By "foreign" it is meant that the polynucleotide or nucleic acid molecule is either heterologous with respect to the host cell, this means derived from a cell or organism with a different genomic background, or is homologous with respect to the host cell but located in a different genomic environment than the naturally occurring counterpart of said nucleic acid molecule. This means that, if the nucleic acid molecule is homologous with respect to the host cell, it is not located in its natural location in the genome of said host cell, in particular it is surrounded by different genes. In this case the polynucleotide may be either under the control of its own promoter or under the control of a heterologous promoter. The above described vector or nucleic acid molecule, which is present in the host cell may either be integrated into the genome of the host cell or it may be maintained in some form extrachromosomally. In this respect, it is also to be understood that the above described nucleic acid molecule can be used to restore or create a mutant gene via homologous recombination.

A mutant of the above mentioned microorganism belonging to the group of lactic acid bacteria, preferably a mutant of the deposited *Lactobacillus* strains, is preferably artificially mutated. In accordance with the present invention, the term "mutated" means (a) permanent modification(s) of genetic material, i.e. nucleic acids, caused, for example, naturally or by physical means or chemical compounds/substances/agents, such as EMS or ENU. Said modifications include point mutations, like transitions or transversions, deletion/insertion/addition of one or more bases within a nucleic acid/gene/chromosome thereby modifying the nucleic acid/gene/chromosome which can cause, inter alis, aberrant gene expression/transcription/translation or inactive gene products, constitutive active/inactive gene products leading to e.g. dominant-negative effects. Preferably, a mutation leads to in increased capability of reducing the peptide concentration in the assay (a) and/or in the assay (A) as described hereinabove. Thus, it is also preferred that the mutant cells of the deposited microorganism which harbor (a) mutation(s) in (a) desired gene(s) or in which (a) mutation(s) in (a) desired gene(s) is induced by methods known to the person skilled in the art. It is also known in the prior art that mutated or genetically engineered bacterial cells can be selected by any suitable method/phenotype. In the context of the present invention, a mutant having an increased capability of reducing the peptide concentration in the assay (a) and/or in the assay (A) as described hereinabove and/or having the capability to stimulate the growth of *Streptococcus mutants* and not to stimulate the growth of *Streptococcus mutans* and/or *Porphyromonas gingivalis* can be tested in accordance with the methods described hereinabove or in the appended Examples. The term "mutant", however, also includes cells of the above mentioned microorganism belonging to the group of lactic acid bacteria, preferably cells of the deposited microorganisms, which harbor naturally-occurring, spontaneous mutations in their genome, i.e. bacterial chromosome. "Spontaneous mutations" are mutations that arise naturally, i.e., without direct genetic manipulation by man, or by exposure to a mutagen. Selection of spontaneous mutants can be accomplished by culturing the strain and selecting the desired variants by, for example, the variant bacterium's capability to show an increased capability of reducing the peptide concentration in the assay (a) and/or in the assay (A) as described hereinabove and/or to stimulate the growth of *Streptococcus mutants* and not to stimulate the growth of *Streptococcus mutans* and/or *Porphyromonas gingivalis*. (see, for example, Sambrook, Russell "Molecular Cloning, A Laboratory Manual", Cold Spring Harbor Laboratory, N.Y. (2001); Ausubel, "Current Protocols in Molecular Biology", Green Publishing Associates and Wiley Interscience, N.Y. (1989)). For example, such mutations may occur during cultivation, for example, during the normal cell division process coupled with DNA replication or during passaging and/or preserving the mutant of the above mentioned microorganism belonging to the group of lactic acid bacteria.

The present invention also relates to a derivative of the above mentioned microorganism belonging to the group of lactic acid bacteria. The term "derivative of the above mentioned microorganism belonging to the group of lactic acid bacteria" includes an inactivated form, an analog or fragment of the above mentioned microorganism belonging to the group of lactic acid bacteria, wherein said inactivated form, analog or fragment retains the capability of reducing the peptide concentration in the assay (a) and/or in the assay (A) as described hereinabove and/or the capability to stimulate the growth of *Streptococcus mutants* and not to stimulate the growth of *Streptococcus mutans* and/or *Porphyromonas gingivalis*.

According to the present invention the term "inactivated form" includes a dead or inactivated cell of the according to the invention which is no longer capable to form a single colony on a plate specific for microorganisms belonging to the genus of *Lactobacillus*. Said dead or inactivated cell may have either an intact or broken cell membrane. Methods for killing or inactivating cells of the above mentioned microorganism belonging to the group of lactic acid bacteria are known in the art. El-Nezami et al., J. Food Prot. 61 (1998), 466-468 describes a method for inactivating *Lactobacillus* species by UV-irradiation. Preferably, the cells of the microorganism according to the invention are thermally inactivated or lyophilised as described in the appended Examples. Lyophilization of the cells as described above has the advantage that they can be easily stored and handled while retaining their capability of reducing the peptide concentration in the assay (a) and/or in the assay (A) as described hereinabove and/or the capability to stimulate the growth of *Streptococcus salivarius* and not to stimulate the growth of *Streptococcus mutans* and/or *Porphyromonas gingivalis*. Moreover, lyophilised cells can be grown again when applied under conditions known in the art to appropriate liquid or solid media. Lyophilization is done by methods known in the art. Preferably, it is carried out for at least 2 hours at room temperature, i.e. any temperature between 16° C. and 25° C. Particularly preferred it is carried out for 16 h under vacuum. Moreover, the lyophilized cells of the above mentioned microorganism belonging to the group of lactic acid bacteria are stable for at least 4 weeks at a temperature of 4° C. so as to still being capable of reducing the peptide concentration in the assay (a) and/or in the assay (A) as described hereinabove and/or of stimulating the growth of Streptococcus mutants and not stimulating the growth of Streptococcus mutans and/or Porphyromonas gingivalis.

Thermal inactivation can be achieved by incubating the cells of the above mentioned microorganism belonging to the group of lactic acid bacteria for at least 10 minutes at a temperature of 80° C. Thermal inactivation can be achieved by autoclaving said cells and or the supernatant at a temperature of 121° C. for at least 20 minutes in the presence of saturated steam at an atmospheric pressure of 2 bar. Preferably, thermal inactivation of the cells or of the culture supernatant is achieved as described herein above in connection with the heat treatment.

In the alternative, thermal inactivation of the cells of the above mentioned microorganism belonging to the group of lactic acid bacteria is achieved by freezing said cells for at least 4 weeks, 3 weeks, 2 weeks, 1 week, 12 hours, 6 hours, 2 hours or 1 hour at −20° C. It is preferred that at least 70%, 75% or 80%, more preferably 85%, 90% or 95% and particularly preferred at least 97%, 98%, 99% and more particularly preferred, 99.1%, 99.2%, 99.3%, 99.4%, 99.5%, 99.6%, 99.7%, 99.8% or 99.9% and most particularly preferred 100% of the cells of the analog of the above mentioned microorganism belonging to the group of lactic acid bacteria are dead or inactivated, however, they have still the capability of reducing the peptide concentration in the assay (a) and/or in the assay (A) as described hereinabove and/or to stimulate the growth of Streptococcus mutants and not to stimulate the growth of Streptococcus mutans and/or Porphyromonas gingivalis. Whether the inactivated form, analog or fragment of the above mentioned microorganism belonging to the group of lactic acid bacteria is indeed dead or inactivated can be tested by methods known in the art, for example, by a test for viability.

The term "inactivated form" or "analog" also encompasses lysates, fractions, such as membrane fractions, or extracts of the above described microorganisms, wherein said lysates, fractions or extracts retain the capability to reduce the peptide concentration in the assay (a) and/or in the assay (A) as described hereinabove and/or to stimulate the growth of Streptococcus mutants and not to stimulate the growth of Streptococcus mutans and/or Porphyromonas gingivalis. These capabilities can be tested as described herein and in particular as described in the appended Examples. In case a lysate, fraction or extract of the microorganism according to the invention, as described herein above, may not show the capability to reduce the peptide concentration in the assay (a) and/or in the assay (A) as described hereinabove and/or to stimulate the growth of Streptococcus mutants and not to stimulate the growth of Streptococcus mutans and/or Porphyromonas gingivalis, then the skilled person can, for example, further purify said lysate, fraction or extract by methods known in the art, which are exemplified herein below, so as to remove substances which inhibit the reduction. Afterwards the person skilled in the art can again test said lysate, fraction or extract whether it is capable of reducing the peptide concentration in the assay (a) and/or in the assay (A) as described hereinabove.

According to the present invention the term "lysate" means a solution or suspension in an aqueous medium of cells of the microorganism according to the invention. However, the term should not be construed in any limiting way. The cell lysate comprises, e.g., macromolecules, like DNA, RNA, proteins, peptides, carbohydrates, lipids and the like and/or micromolecules, like amino acids, sugars, lipid acids and the like, or fractions of it. Additionally, said lysate comprises cell debris which may be of smooth or granular structure. Preferably, said lysate comprises the cell wall or the cell membrane or both or portions or fragments of the cell wall or the cell membrane or of both. Methods for preparing cell lysates of microorganism are known in the art, for example, by employing French press, cells mill using glass or iron beads or enzymatic cell lysis and the like. In addition, lysing cells relates to various methods known in the art for opening/destroying cells. The method for lysing a cell is not important and any method that can achieve lysis of the cells of the above mentioned microorganism belonging to the group of lactic acid bacteria may be employed. An appropriate one can be chosen by the person skilled in the art, e.g. opening/destruction of cells can be done enzymatically, chemically or physically. Non-limiting examples for enzymes and enzyme cocktails are proteases, like proteinase K, lipases or glycosidases; non-limiting examples for chemicals are ionophores, detergents, like sodium dodecyl sulfate, acids or bases; and non-limiting examples of physical means are high pressure, like French-pressing, osmolarity, temperature, like heat or cold. Additionally, a method employing an appropriate combination of an enzyme other than the proteolytic enzyme, an acid, a base and the like may also be utilized. For example, the cells of the above mentioned microorganism belonging to the group of lactic acid bacteria are lysed by freezing and thawing, more preferably freezing at temperatures below −70° C. and thawing at temperatures of more than 30° C., particularly freezing is preferred at temperatures below −75° C. and thawing is preferred at temperatures of more than 35° C. and most preferred are temperatures for freezing below −80° C. and temperatures for thawing of more than 37° C. It is also preferred that said freezing/thawing is repeated for at least 1 time, more preferably for at least 2 times, even more preferred for at least 3 times, particularly preferred for at least 4 times and most preferred for at least 5 times.

Accordingly, those skilled in the art can prepare the desired lysates by referring to the above general explanations, and appropriately modifying or altering those methods, if necessary. Preferably, the aqueous medium used for the lysates as described is water, physiological saline, or a buffer solution. An advantage of a bacterial cell lysate is that it can be easily produced and stored cost efficiently since less technical facilities are needed.

Preferably, the term "extract" means a subcellular component of the above mentioned microorganism belonging to the group of lactic acid bacteria, e.g., a macromolecule, like a protein, DNA, RNA, a peptide, a carbohydrate, a lipid and the like and/or a micromolecule, like an amino acid, a sugar, a lipid acid and the like or any other organic compound or molecule, or a combination of said macromolecules and/or micromolecules or any fraction of it, wherein said extract retains the capability to reduce the peptide concentration in the assay (a) and/or in the assay (A) as described hereinabove and/or to stimulate the growth of Streptococcus mutants and not to stimulate the growth of Streptococcus mutans and/or Porphyromonas gingivalis. These properties can be tested as described herein and in particular as described in the appended Examples. Preferably, said extract comprises the cell wall or the cell membrane or both or portions or fragments of the cell wall or the cell membrane or of both. More preferably, the term "extract" refers to any of the above described subcellular components in a cell-free medium.

In a further preferred embodiment an extract may be obtained by lysing cells according to various methods known in the art for opening/destroying cells, as described herein above and/or as supernatant of a centrifugation procedure of a culture of the above mentioned microorganism belonging to the group of lactic acid bacteria in any appropriate liquid, medium or buffer known to the person skilled in the art or of a lysate of such a culture or any other suitable cell suspension. More preferably, the extract may be a purified lysate or cell culture supernatant or any fraction or subportion thereof, wherein said purified lysate or cell culture supernatant or any fraction or subportion thereof retains the capability to reduce the peptide concentration in the assay (a) and/or in the assay (A) as described hereinabove and/or to stimulate the growth of *Streptococcus mutants* and not to stimulate the growth of *Streptococcus mutants* and/or *Porphyromonas gingivalis*. These properties can be tested as described herein and in particular as described in the appended Examples. Suitable methods for fractionation and purification of a lysate, culture supernatant or an extract are known to the person skilled in the art and comprise, for example, affinity chromatography, ion-exchange chromatography, size-exclusion chromatography, reversed phase-chromatography, and chromatography with other chromatographic material in column or batch methods, other fractionation methods, e.g., filtration methods, e.g., ultrafiltration, dialysis, dialysis and concentration with size-exclusion in centrifugation, centrifugation in density-gradients or step matrices, precipitation, e.g., affinity precipitations, salting-in or salting-out (ammoniumsulfate-precipitation), alcoholic precipitations or any other suitable proteinchemical, molecular biological, biochemical, immunological, chemical or physical method.

According to the invention, lysates are also preparations of fractions of molecules from the above-mentioned lysates. These fractions can be obtained by methods known to those skilled in the art, e.g., chromatography, including, e.g., affinity chromatography, ion-exchange chromatography, size-exclusion chromatography, reversed phase-chromatography, and chromatography with other chromatographic material in column or batch methods, other fractionation methods, e.g., filtration methods, e.g., ultrafiltration, dialysis, dialysis and concentration with size-exclusion in centrifugation, centrifugation in density-gradients or step matrices, precipitation, e.g., affinity precipitations, salting-in or salting-out (ammoniumsulfate-precipitation), alcoholic precipitations or other proteinchemical, molecular biological, biochemical, immunological, chemical or physical methods to separate above components of the lysates. In a preferred embodiment those fractions, which are more immunogenic than others are preferred. Those skilled in the art are able to choose a suitable method and determine its immunogenic potential by referring to the above general explanations and specific explanations in the examples herein, and appropriately modifying or altering those methods, if necessary.

Accordingly, the term "inactivated form or analog" also encompasses filtrates of the microorganism of the invention, wherein said filtrates preferably retain the capability to reduce the peptide concentration in the assay (a) and/or in the assay (A) as described hereinabove and/or to stimulate the growth of *Streptococcus mutants* and not to stimulate the growth of *Streptococcus mutants* and/or *Porphyromonas gingivalis*. These properties can be tested as described herein and in particular as described in the appended Examples. In case, a filtrate of the above mentioned microorganism belonging to the group of lactic acid bacteria, as described herein above, may not have the capability to reduce the peptide concentration in the assay (a) and/or in the assay (A) as described hereinabove and/or to stimulate the growth of *Streptococcus mutants* and not to stimulate the growth of *Streptococcus mutants* and/or *Porphyromonas gingivalis*, then the skilled person can, for example, further purify said filtrate by methods known in the art, which are exemplified herein below, so as to remove substances which inhibit the reduction and/or growth stimulation. Afterwards the person skilled in the art can again test said filtrate whether it is capable of reducing the peptide concentration in the assay (a) and/or in the assay (A) as described hereinabove and/or of stimulating the growth of *Streptococcus salivarius* and not stimulating the growth of *Streptococcus mutans* and/or *Porphyromonas gingivalis*.

The term "filtrate" also means a cell-free solution or suspension of the microorganism of the invention, as described herein above which has been obtained as supernatant of a centrifugation procedure of a culture of the above mentioned microorganism belonging to the group of lactic acid bacteria in any appropriate liquid, medium or buffer known to the person skilled in the art. However, the term should not be construed in any limiting way. The filtrate comprises, e.g., macromolecules, like DNA, RNA, proteins, peptides, carbohydrates, lipids and the like and/or micromolecules, like amino acids, sugars, lipid acids and the like, or fractions of it. Methods for preparing filtrates of microorganisms are known in the art. In addition, "filtrate" relates to various methods known in the art. The exact method is not important and any method that can achieve filtration of the cells of the microorganism of the invention, as described herein above, may be employed. The term filtrate also includes culture supernatants, e.g. obtained by pelleting the cells by centrifugation and recovering the resulting supernatant.

In a particularly preferred embodiment the filtrate, most preferably the culture supernatant, is further treated, in particular by heat or by lyophilisation as described herein above.

A "fragment" of the microorganism according to the invention encompasses any part of the cells of the above mentioned microorganism belonging to the group of lactic acid bacteria. Preferably, said fragment is a membrane fraction obtained by a membrane-preparation. Membrane preparations of microorganisms belonging to the genus of *Lactobacillus* can be obtained by methods known in the art, for example, by employing the method described in Rollan et al., Int. J. Food Microbiol. 70 (2001), 303-307, Matsuguchi et al., Clin. Diagn. Lab. Immunol. 10 (2003), 259-266 or Stentz et al., Appl. Environ. Microbiol. 66 (2000), 4272-4278 or Varmanen et al., J. Bacteriology 182 (2000), 146-154. Alternatively, a whole cell preparation is also envisaged. Preferably, the herein described derivative or fragment of the above mentioned microorganism belonging to the group of lactic acid bacteria retains the capability to reduce the peptide concentration in the assay (a) and/or in the assay (A) as described hereinabove and/or to stimulate the growth of *Streptococcus salivarius* and not to stimulate the growth of *Streptococcus mutans* and/or *Porphyromonas gingivalis*.

The present invention also relates to a composition comprising the above mentioned microorganism according to the present invention, inactivated form, derivative or mutant or an analog or fragment thereof. The composition is preferably a cosmetic composition or a pharmaceutical composition, for example for the treatment and/or prevention of oral malodour and/or halitosis, or a feed or food composition.

In a preferred embodiment, said composition comprises a microorganism as described above in an amount between $10^2$ to $10^{12}$ cells, preferably $10^3$ to $10^8$ cells per mg in a solid form of the composition. In case of a liquid form of compositions, the amount of the microorganisms is between $10^2$ to $10^{13}$ cells per ml. However, for specific compositions the amount of the microorganism may be different as is described herein.

The cosmetical composition may comprise a cosmetically or orally acceptable carrier or excipient. The pharmaceutical composition may comprise a pharmaceutically or orally acceptable carrier or excipient. The feed or food composition may comprise an orally acceptable carrier or excipient.

The present invention also relates to the use of a microorganism according to the present invention, inactivated form, derivative or mutant or an analog or fragment thereof for the preparation of a composition comprising the above mentioned microorganism according to the present invention, inactivated form, derivative or mutant or an analog or fragment thereof, in particular a cosmetic composition, a feed or food composition or a pharmaceutical composition for the prevention and/or treatment of oral malodour and/or halitosis.

Such a composition may be produced by a method comprising the step of formulating a microorganism according to the invention with a cosmetically, orally or pharmaceutical acceptable carrier or excipient.

The term "composition", as used in accordance with the present invention, relates to (a) composition(s), which comprise(s) at least one microorganism or mutant or derivative as described above or an inactivated form or analog or fragment of said microorganism. It is envisaged that the compositions as used in accordance with the present invention, which are described herein below comprise the aforementioned ingredients in any combination. It may, optionally, comprise at least one further ingredient suitable for preventing and/or oral malodour and/or halitosis. Accordingly, it may optionally comprise any combination of the hereinafter described further ingredients. The term "ingredients suitable for preventing and/or oral malodour and/or halitosis" encompasses compounds or compositions and/or combinations thereof which are known in the art to reduce oral malodour. Examples are metal salts, such as zinc chloride, or disinfectants, such as alcohol or chlorhexidine, which are used to treat the tongue. Another example are compounds which help to maintain the pH of saliva at a physiologically normal level. These may be substances having a pH-rising or pH-buffering effect (e.g. bicarbonates, carbamides, phosphates, proteins and/or salts). It is known that microbial species associated with caries and mucosal infections favour an acid pH; microbial species associated with the development of periodontal disease favour a pH above normal, whereas microbial species associated with good oral health favour a neutral pH. A further example are probiotic bacteria (e.g. *Lactobacillus* and *Streptococcus*) as disclosed in US200707137, US2006018843 or WO2007/077210 or lactic acid bacteria belonging to the genus *Weissella*, that inhibit the growth of VSC-producing bacteria by interacting with them and generating hydrogen peroxide under aerobic and anaerobic conditions as described in US2006045870. Finally, BLIS (bacteriocin-like inhibitory substances)-producing *Streptococcus mutants* strains and extracts thereof could be mentioned in this context (US2006171901).

It is noted that the composition as used in accordance with the present invention may optionally comprise one or more of the aforementioned optional ingredients which are suitable for preventing and/or oral malodour and/or halitosis. Thus, said composition may contain at least two, three, four, five, etc., i.e. "n" optional ingredients, wherein "n" is an integer greater than 2 which is not limited. Said optional ingredients may be combined in any possible combination.

The composition may be in solid, liquid or gaseous form and may be, inter alia, in the form of (a) powder(s), (a) tablet(s), (a) film preparation(s), (a) solution(s) (an) aerosol(s), granules, pills, suspensions, emulsions, capsules, syrups, liquids, elixirs, extracts, tincture or fluid extracts or in a form which is particularly suitable for oral administration.

Liquid preparations suitable for oral administration, for example syrups can be prepared, using water, conventional saccharides such as sucrose, sorbitol and fructose, glycols such as polyethylene glycol and propylene glycol, oils such as sesame seed oil, olive oil and soybean oil, antiseptics such as p-hydroxybenzoate ester, preservatives such as p-hydroxybenzoate derivatives, for example p-hydroxybenzoate methyl and sodium benzoate, and other materials such as flavors, for example strawberry flavor or peppermint.

Further, preparations suitable for oral administration, for example tablets, powders and granules can be produced, using conventional saccharides such as sucrose, glucose, mannitol, and sorbitol, starch such as potato, wheat and corn, inorganic materials such as calcium carbonate, calcium sulfate, sodium hydrogen carbonate, and sodium chloride, plant powders such as crystal cellulose, licorice powder and gentian powder, excipients such as pinedex, disintegrators such as starch, agar, gelatin powder, crystal cellulose, carmellose sodium, carmellose calcium, calcium carbonate, sodium hydrogen carbonate and sodium alginate, lubricants such as magnesium stearate, talc, hydrogenated vegetable oils, macrogol, and silicone oil, binders such as polyvinyl alcohol, hydroxypropyl cellulose, methyl cellulose, ethyl cellulose, carmellose, gelatin, and starch glue fluid, surfactants such as fatty acid ester, and plasticizers such as glycerin. A film preparation(s) can be prepared by methods known in the art. An example for the preparation of a film is given in Example 19 herein.

In case of ordinary oral administration, the dose of the above described microorganism or analog or fragment could be (in dry weight) as described hereinabove with respect to the cell number or with respect to the mass, for example, 1 µg to 50 g, 1 µg to 10 g, 1 µg to 5 mg, 1 µg to 1 mg or any other weight per subject per day or in several portions daily. In case of dosing to non-human animals, further, the dose varies depending on the age and species of an animal and the nature or severity of the symptom thereof. Without any specific limitation, the dose for animals is 0.1 mg to 10 g per 1 kg body weight, preferably 1 mg to 1 g per 1 kg body weight once daily or in several portions daily. However, these doses and the number of dosages vary depending on the individual conditions.

Preferably, the composition in accordance with the present invention is a cosmetic composition further comprising a cosmetically acceptable carrier or excipient. More preferably, said composition is a dentifrice, chewing gum, lozenge, mouth wash, mouse rinse, dental floss or dental tape.

The cosmetic composition in accordance with the present invention comprises the microorganism, inactivated form, mutant, derivative, analog or fragment thereof as described above in connection with the composition of the invention and further a cosmetically or orally acceptable carrier. Preferably, as mentioned in connection with the composition in accordance with the present invention the microorganism, inactivated form, mutant, derivative, analog or fragment thereof is a microorganism, inactivated form, mutant, derivative, analog or fragment as described herein above. Preferably the cosmetic composition according to the present invention is for use in oral applications. Accordingly, it may be in the form of a toothpaste, dentifrice, tooth powder, topical oral gel, mouth rinse, denture product, mouthspray, lozenge, oral tablet, chewing gum, dental floss or dental tape.

The term "orally or cosmetically acceptable carrier" as used herein means a suitable vehicle, which can be used to apply the present compositions to the oral cavity in a safe and effective manner. Such vehicle may include materials such as fluoride ion sources, additional anticalculus agents, buffers, other abrasive materials, peroxide sources, alkali metal bicarbonate salts, thickening materials, humectants, water, surfactants, titanium dioxide, flavor system, sweetening agents, xylitol, coloring agents, and mixtures thereof. The term "safe and effective amount" as used herein, means a sufficient amount to clean teeth and reduce stain/plaque/gingivitis/calculus without harming the tissues and structures of the oral cavity.

The pH of the present herein described compositions ranges preferably from about 3.0 to about 9.0, with the preferred pH being from about 5.5 to about 9.0 and the most preferred pH being 7.0 to about 8.5 or 9.0.

The cosmetic composition is a product, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity. The oral composition may be a single phase oral composition or may be a combination of two or more oral compositions.

The term "dentifrice", as used herein, means paste, gel, or liquid formulations unless otherwise specified. The dentifrice composition may be in any desired form, such as deep striped, surface striped, multilayered, having the gel surrounding the paste, or any combination thereof. The dentifrice composition may be contained in a physically separated compartment of a dispenser and dispensed side-by-side. Dentifrice compositions are, for example, described in EP-B1 0 617 608.

Preferred dentifrice compositions are described in Examples 13 to 16. In addition to the above described components, the dentifrice compositions of this invention can contain a variety of optional dentifrice ingredients some of which are described below. Optional ingredients include, for example, but are not limited to, adhesives, sudsing agents, flavouring agents, sweetening agents, additional antiplaque agents, additional abrasives, and colouring agents. These and other optional components are further described, for example, in U.S. Pat. Nos. 5,004,597; 4,885,155; 3,959,458; and 3,937,807.

For example, the toothpaste may include surfactants, chelating agents, fluoride sources, teeth whitening actives and teeth color modifying substances, thickening agents, humectants, flavouring and sweetening agents, alkali metal bicarbonate salt, miscellaneous carriers and/or other active agents.

One of the preferred optional agents as used in accordance with the present invention is a surfactant, preferably one selected from the group consisting of sarcosinate surfactants, isethionate surfactants and taurate surfactants. Preferred for use herein are alkali metal or ammonium salts of these surfactants. Most preferred herein are the sodium and potassium salts of the following: lauroyl sarcosinate, myristoyl sarcosinate, palmitoyl sarcosinate, stearoyl sarcosinate and oleoyl sarcosinate.

Another preferred optional agent is a chelating agent such as tartaric acid and pharmaceutically-acceptable salts thereof, citric acid and alkali metal citrates and mixtures thereof. Chelating agents are able to complex calcium found in the cell walls of the bacteria. Chelating agents can also disrupt plaque by removing calcium from the calcium bridges, which help hold this biomass intact.

It is common to have an additional water-soluble fluoride compound present in dentifrices and other oral compositions in an amount sufficient to give a fluoride ion concentration in the composition at 25° C., and/or when it is used of from about 0.0025% to about 5.0% by weight, preferably from about 0.005% to about 2.0% by weight, to provide anticaries effectiveness. A wide variety of fluoride ion-yielding materials can be employed as sources of soluble fluoride in the present compositions. Examples of suitable fluoride ion-yielding materials are found in U.S. Pat. Nos. 3,535,421 and 3,678,154. Representative fluoride ion sources include stannous fluoride, sodium fluoride, potassium fluoride, sodium monofluorophosphate and many others. Stannous fluoride and sodium fluoride are particularly preferred, as well as mixtures thereof.

The oral care compositions as of the present invention may also comprise teeth whitening actives, including bleaching or oxidizing agents such as peroxides, perborates, percarbonates, peroxyacids, persulfates, metal chlorites, and combinations thereof. Suitable peroxide compounds include hydrogen peroxide, urea peroxide, calcium peroxide, and mixtures thereof. A preferred percarbonate is sodium percarbonate. Other suitable whitening agents include potassium, ammonium, sodium and lithium persulfates and perborate mono- and tetrahydrates, and sodium pyrophosphate peroxyhydrate. Suitable metal chlorites include calcium chlorite, barium chlorite, magnesium chlorite, lithium chlorite, sodium chlorite, and potassium chlorite. The preferred chlorite is sodium chlorite. Additional whitening actives may be hypochlorite and chlorine dioxide.

In addition to bleaching agents as teeth whitening agents, teeth color modifying substances may be considered among the oral care actives useful in the present invention. These substances are suitable for modifying the color of the teeth to satisfy the consumer. These substances comprise particles that when applied on the tooth surface modify that surface in terms of absorption and, or reflection of light. Such particles provide an appearance benefit when a film containing such particles is applied over the surfaces of a tooth or teeth.

In preparing toothpaste or gels, it is necessary to add some thickening material to provide a desirable consistency of the composition, to provide desirable active release characteristics upon use, to provide shelf stability, and to provide stability of the composition, etc. Preferred thickening agents are carboxyvinyl polymers, carrageenan, hydroxyethyl cellulose, laponite and water soluble salts of cellulose ethers such as sodium carboxymethylcellulose and sodium carboxymethyl hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture.

Another optional component of the topical, oral carriers of the compositions of the subject invention is a humectant. The humectant serves to keep toothpaste compositions from hardening upon exposure to air, to give compositions a moist feel to the mouth, and, for particular humectants, to impart desirable sweetness of flavor to toothpaste compositions. The humectant, on a pure humectant basis, generally comprises from about 0% to about 70%, preferably from about 5% to about 25%, by weight of the compositions herein. Suitable humectants for use in compositions of the subject invention include edible polyhydric alcohols such as glycerin, sorbitol, xylitol, butylene glycol, polyethylene glycol, and propylene glycol, especially sorbitol and glycerin.

Flavoring and sweetening agents can also be added to the compositions. Suitable flavoring agents include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal known as CGA, and mixtures thereof. Flavouring agents are generally used in the compositions at levels of from about 0.001% to about 5%, by weight of the composition.

Sweetening agents which can be used include sucrose, glucose, saccharin, dextrose, levulose, lactose as described herein above, mannitol, sorbitol, fructose, maltose, xylitol, saccharin salts, thaumatin, aspartame, D-tryptophane, dihydrochalcones, acesulfame and cyclamate salts, especially sodium cyclamate and sodium saccharin, and mixtures thereof. A composition preferably contains from about 0.1% to about 10% of these agents, preferably from about 0.1% to about 1%, by weight of the composition.

The composition of the present invention may also include an alkali metal bicarbonate salt. Alkali metal bicarbonate salts are soluble in water and unless stabilized, tend to release carbon dioxide in an aqueous system. Sodium bicarbonate, also known as baking soda, is the preferred alkali metal bicarbonate salt. The present composition may contain from about 0.5% to about 30%, preferably from about 0.5% to about 15%, and most preferably from about 0.5% to about 5% of an alkali metal bicarbonate salt.

Water employed in the preparation of commercially suitable oral compositions should preferably be of low ion content and free of organic impurities. Water generally comprises from about 10% to about 50%, and preferably from about 20% to about 40%, by weight of the aqueous toothpaste compositions herein. These amounts of water include the free water which is added plus that which is introduced with other materials, such as with sorbitol. Titanium dioxide may also be added to the present composition. Titanium dioxide is a white powder, which adds opacity to the compositions. Titanium dioxide generally comprises from about 0.25% to about 5% by weight of the dentifrice compositions.

The pH of the compositions of the invention is preferably adjusted through the use of buffering agents. Buffering agents, as used herein, refer to agents that can be used to adjust the pH of the compositions to a range of about 4.5 to about 9.5. Buffering agents include monosodium phosphate, trisodium phosphate, sodium hydroxide, sodium carbonate, sodium acid pyrophosphate, citric acid, and sodium citrate. Buffering agents can be administered at a level of from about 0.5% to about 10%, by weight of the present compositions. The pH of dentifrice compositions is measured from a 3:1 aqueous slurry of dentifrice, e.g., 3 parts water to 1 part toothpaste.

Other optional agents that may be used in the present compositions include dimethicone copolyols selected from alkyl- and alkoxy-dimethicone copolyols, such as C12 to C20 alkyl dimethicone copolyols and mixtures thereof. Highly preferred is cetyl dimethicone copolyol marketed under the Trade Name Abil EM90. The dimethicone copolyol is generally present in a level of from about 0.01% to about 25%, preferably from about 0.1% to about 5%, more preferably from about 0.5% to about 1.5% by weight. The dimethicone copolyols aid in providing positive tooth feel benefits. Other useful carriers include biphasic dentifrice formulations such as those disclosed in U.S. Pat. Nos. 5,213,790; 5,145,666; 5,281,410; 4,849,213 and 4,528,180.

The cosmetic composition may also include other active agents, such as antimicrobial agents. Included among such agents are water insoluble non-cationic antimicrobial agents such as halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, and halogenated carbanilides. The water soluble antimicrobials include quaternary ammonium salts and bis-biquanide salts, among others. Triclosan monophosphate is an additional water soluble antimicrobial agent. The quaternary ammonium agents include those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl(2-phenoxyethyl)ammonium bromide, benzyl dimethylstearyl ammonium chloride, cetyl pyridinium chloride, quaternized 5-amino-1,3-bis(2-ethylhexyl)-5-methyl hexa hydropyrimidine, benzalkonium chloride, benzethonium chloride and methyl benzethonium chloride are exemplary of typical quaternary ammonium antibacterial agents. Other compounds are bis[4-(R-amino)-1-pyridinium]alkanes as disclosed in U.S. Pat. No. 4,206.215. Other antimicrobials such as copper bisglycinate, copper glysinate, zinc citrate, and zinc lactate may also be included. Enzymes are another type of active that may be used in the present compositions. Useful enzymes include those that belong to the category of proteases, lytic enzymes, plaque matrix inhibitors and oxidases: Proteases include papain, pepsin, trypsin, ficin, bromelin; cell wall lytic enzymes include lysozyme; plaque matrix inhibitors include dextranses, mutanases; and oxidases include glucose oxidase, lactate oxidase, galactose oxidase, uric acid oxidase, peroxidases including horse radish peroxidase, myeloperoxidase, lactoperoxidase, chloroperoxidase. The oxidases also have whitening/cleaning activity, in addition to anti-microbial properties. Such agents are disclosed in U.S. Pat. No. 2,946,725 and in U.S. Pat. No. 4,051,234. Other antimicrobial agents include chlorhexidine, triclosan, triclosan monophosphate, and flavor oils such as thymol. Triclosan and other agents of this type are disclosed in U.S. Pat. Nos. 5,015,466 and 4,894,220. These agents, which provide anti-plaque benefits, may be present at levels of from about 0.01% to about 5.0%, by weight of the dentifrice composition.

The term "chewing gum" as defined herein means a confectionery composition which is suitable for chewing and which comprises any suitable amount of elastomer, known to the person skilled in the art, preferably an amount of 2% or greater, by weight of the composition. Suitable lozenge and chewing gum components are, for example, disclosed in U.S. Pat. Nos. 4,083,955; 6,770,264 or 6,270,781. Preferred lozenges are those described in Examples 11 and 12. A preferred chewing gum composition is described in Example 17.

Compositions according to the present invention preferably comprise an elastomer, or mixture of several different elastomers. Elastomeric materials are generally known in the art but illustrative examples include styrene-butadiene rubber (SBR); synthetic gums; polyisobutylene and isobutylene-isoprene copolymers; natural gums; chicle; natural rubber; jelutong; balata; guttapercha; lechi caspi; sorva; and mixtures thereof. Compositions of the present invention preferably comprise from about 2% to about 30%, more preferably from about 5% to about 25%, by weight, of elastomer. These levels are determined by the desired final texture of the chewing gum since when the total level of elastomer is below about 2% the base composition lacks elasticity, chewing texture, and cohesiveness whereas at levels above about 30% the formulation is hard, rubbery and maintains a tight chew. Elastomer solvents are also preferably present in compositions of the present invention since they aid softening of the elastomer component. Preferred examples of elastomer solvents for use herein include the pentaerythritol ester of partially hydrogenated wood rosin, pentaerythritol ester of wood rosin, glycerol ester of partially dimerized rosin, glycerol ester of polymerised rosin, glycerol ester of tall oil, wood or gum rosin, glycerol ester of partially hydrogenated rosin, methyl ester of partially hydrogenated rosin, and mixtures thereof. Compositions of the present invention preferably comprise from about 2% to about 50%, more preferably from about 10% to about 35%, by weight, of elastomer solvent.

Lozenges according to the present invention can be prepared, for example, by art-recognized techniques for forming compressed tablets where the disaccharide is dispersed on a compressible solid carrier, optionally combined with any appropriate tableting aids such as a lubricant (e.g., magnesium-stearate) and is compressed into tablets. The solid carrier component for such tableting formulations can be a saliva-soluble solid, such as a cold water-soluble starch or a monosaccharide, so that the lozenge will readily dissolve in the mouth to release the contained disaccharide acid in saliva solution for contact with and absorption by the oral/pharyngeal mucosa when the lozenge is held in the mouth. The pH of the above-described formulations can range from about 4 to about 8.5.

Lozenges according to the present invention can also be prepared utilizing other art-recognized solid unitary dosage formulation techniques.

A mouth wash or mouth rinse according to the present invention could preferably be as follows:

| A | Olium menthae | 1.2 parts |
|---|---|---|
|  | Tinctura Arnicae | 3.0 parts |
|  | Tinctura Myrrhae | 3.0 parts |
|  | Tween | 5.0 parts |
| B | Spiritus 90% | 50.0 parts |
| C | Sodium Benzoate | 0.2 parts |
|  | Sweetening agent (e.g. aspartane) | 0.02 parts |
|  | Agua destilata ad 100, |  |

A is to be well mixed, B is added under stirring and C is added subsequently. The resulting clear liquid is to be filtered within 48 hours after preparation. Another preferred mouth wash is described in Example 18.

Regardless of the dosage form, liquid or solid, in one preferred embodiment of the present invention the dosage form is held in the patient's mouth for a period of time to promote contact of the microorganism or analog or fragment of an above mentioned microorganism belonging to the group of lactic acid bacteria with the patient's oral cavity.

The terms "dental floss" and "dental tape" as used herein refer to a material to dislodge and remove decomposing food material that accumulated at interproximal and subgingival surfaces and to dislodge and remove bacteria, plaque and/or calculus that accumulated in the oral cavity. The dental floss or dental tape may further contain, in addition to the microorganisms according to the present invention as described herein above, cleaners, abrasives, tartar control ingredients, whiteners, surfactants and/or active ingredients like fluorides, antimicrobials, chemotherapeutic agents or antibiotics. Further additional agents are antiplaque agents, flavouring agents and colouring agents. The dental floss or dental tape may be in any suitable form, known to the person skilled in the art, for example, in the form of PTFE (Teflon) dental flosses as described, for instance, in U.S. Pat. Nos. 3,664,915, 3,953,566, 3,962,153, 4,096,227, 4,187,390, 4,256,806, 4,385,093, 4,478.665, 4,776,358, 5,033,488, 5,209,251, 5,220,932, 5,518,012, 5,718,251, 5,765,576 or 5,911,228, in the form of monofilament interproximal devices as described, for instance, in U.S. Pat. Nos. 3,800,812, 4,974,615, 5,760,117, 5,433,226, 5,479,952, 5,503,842, 5,755,243, 5,884,639, 6,003,525 or 6,027,592, or in the form of biocomponent tapes. Preferably, the dental floss or dental tape may be in the form of an elastomeric coated monofilament as described, for instance, in US 20050226820 or in the form of an oriented thermoplastic based dental tape as described, for instance, in US 20020144704.

The cosmetic compositions as described herein above may be used in the ambit of human oral administration as well as in the ambit of veterinary oral administration, preferably for non-human mammals, more preferably for pets. If the cosmetic composition is used in the ambit of veterinary oral administration, the composition may contain further ingredients suitable for such an administration, as known by a person skilled in the art.

The present invention also relates to the use of a microorganism according to the invention or of an inactivated form thereof for the preparation of a pharmaceutical composition for the treatment and/or prophylaxis of oral malodour and/or halitosis. Preferably, the pharmaceutical composition further comprises a pharmaceutical acceptable carrier or excipient.

Pharmaceutical compositions comprise a therapeutically effective amount of the microorganism of the present invention and can be formulated in various forms, e.g. in solid, liquid, powder, aqueous, lyophilized form. U.S. Pat. No. The pharmaceutical composition may be administered with a pharmaceutically acceptable carrier to a patient, as described herein. In a specific embodiment, the term "pharmaceutically acceptable" means approved by a regulatory agency or other generally recognized pharmacopoeia for use in animals, and more particularly in humans.

The term "carrier" refers to a diluent, adjuvant, excipient, or vehicle with which the therapeutic is administered. Such a carrier is pharmaceutically acceptable, i.e. is non-toxic to a recipient at the dosage and concentration employed. It is preferably isotonic, hypotonic or weakly hypertonic and has a relatively low ionic strength, such as provided by a sucrose solution. Such pharmaceutical carriers can be sterile liquids, such as water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. Suitable pharmaceutical excipients include starch, glucose, sucrose, gelatin, malt, rice, flour, chalk, silica gel, sodium stearate, glycerol monostearate, talc, sodium ion, dried skim milk, glycerol, propylene, glycol, water, ethanol and the like. The excipient may contain lactose as described herein above, most preferably it is lactose-free. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, starch, magnesium stearate, sodium saccharine, cellulose, magnesium carbonate, etc. Examples of suitable pharmaceutical carriers are described in "Remington's Pharmaceutical Sciences" by E. W. Martin. Skim milk, skim milk powder, non-milk or non-lactose containing products may also be employed. The skim milk powder is conventionally suspended in phosphate buffered saline (PBS), autoclaved or filtered to eradicate proteinaceous and living contaminants, then freeze dried heat dried, vacuum dried, or lyophilized. Some other examples of substances which can serve as pharmaceutical carriers are sugars, such as glucose and sucrose; starches such as corn starch and potato starch; cellulose and its derivatives such as sodium carboxymethycellulose, ethylcellulose and cellulose acetates; powdered tragancanth; malt; gelatin; talc; stearic acids; magnesium stearate; calcium sulfate; calcium carbonate; vegetable oils, such as peanut oils, cotton seed oil, sesame oil, olive oil, corn oil and oil of theobroma; polyols such as propylene glycol, glycerine, sorbitol, manitol, and polyethylene glycol; agar; alginic acids; pyrogen-free water; isotonic saline; cranberry extracts and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as colouring agents, flavouring agents, lubricants, excipients, tabletting agents, stabilizers, anti-oxidants and preservatives, can also be present.

Various carriers and/or excipients suitable for oral administration which are well known in the art may be used for the purpose of this invention. The composition may, if desired, further contain various known additives such as, for example, preservatives, hardening agents, lubricants, emulsifiers, stabilizers, essence and the like. Such compositions will contain a therapeutically effective amount of the aforementioned compounds, preferably in purified form, together with a suitable amount of carrier so as to provide the form for proper administration to the patient. The formulation should suit the mode of administration.

Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline.

The pharmaceutical composition of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

In vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems. Preferably, the pharmaceutical composition is administered directly or in combination with an adjuvant. Adjuvants may be selected from the group consisting of a chloroquine, protic polar compounds, such as propylene glycol, polyethylene glycol, glycerol, EtOH, 1-methyl L-2-pyrrolidone or their derivatives, or aprotic polar compounds such as dimethylsulfoxide (DMSO), diethylsulfoxide, di-n-propylsulfoxide, dimethylsulfone, sulfolane, dimethylformamide, dimethylacetamide, tetramethylurea, acetonitrile or their derivatives. These compounds are added in conditions respecting pH limitations. The composition as used in accordance with the present invention can be administered to a vertebrate. "Vertebrate" as used herein is intended to have the same meaning as commonly understood by one of ordinary skill in the art. Particularly, "vertebrate" encompasses mammals, and more particularly humans.

The term "administered" means administration of a therapeutically effective dose of the aforementioned composition. By "therapeutically effective amount" is meant a dose that produces the effects for which it is administered, preferably this effect is anticariogenic. The exact dose will depend on the purpose of the treatment, and will be ascertainable by one skilled in the art using known techniques. As is known in the art and described above, adjustments for systemic versus localized delivery, age, body weight, general health, sex, diet, time of administration, drug interaction and the severity of the condition may be necessary, and will be ascertainable with routine experimentation by those skilled in the art.

The methods are applicable to both human therapy and veterinary applications. The compounds described herein having the desired therapeutic activity may be administered in a physiologically acceptable carrier to a patient, as described herein. Depending upon the manner of introduction, the compounds may be formulated in a variety of ways as discussed below. The concentration of therapeutically active compound in the formulation may vary from about 0.1-100 wt %. The agents maybe administered alone or in combination with other treatments.

The administration of the pharmaceutical composition can be done in a variety of ways as discussed above, including, but not limited to, orally, subcutaneously, intravenously, intraarterial, intranodal, intramedullary, intrathecal, intraventricular, intranasally, intrabronchial, transdermally, intranodally, intrarectally, intraperitoneally, intramuscularly, intrapulmonary, vaginally, rectally, or intraocularly.

Preferably the administration is orally or buccal. The attending physician and clinical factors will determine the dosage regimen. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 µg; however, doses below or above this exemplary range are envisioned, especially considering the aforementioned factors.

The dosages are preferably given once a week, however, during progression of the treatment the dosages can be given in much longer time intervals and in need can be given in much shorter time intervals, e.g., daily. In a preferred case the immune response is monitored using herein described methods and further methods known to those skilled in the art and dosages are optimized, e.g., in time, amount and/or composition. Progress can be monitored by periodic assessment. The pharmaceutical composition of the invention may be administered locally or systemically. It is also envisaged that the pharmaceutical compositions are employed in co-therapy approaches, i.e. in co-administration with other medicaments or drugs, for example other drugs for preventing, treating or ameliorating caries, which are described herein.

In another preferred embodiment the present invention relates to the use of a microorganism according to the present invention for the preparation of a composition for the treatment and/or prophylaxis of oral malodour and/or halitosis, wherein the composition is a foodstuff or feedstuff and to a foodstuff or feedstuff comprising a microorganism according to the present invention, inactivated form thereof, mutant, derivative, analog or fragment. Preferably a composition in the form of a foodstuff or feedstuff is a food or feed composition comprising a microorganim, inactivated form, mutant, derivative, analog or fragment thereof as described herein above further comprising an orally acceptable carrier or excipient.

"Food" or "feed" comprises any edible, palatable and/or drinkable stuff for mammals, for example, humans or animals, e.g., pets as described herein. Food and feedstuff is described herein elsewhere. An "orally acceptable carrier" is described herein above and is preferably not toxic and of food and/or feed grade. Yet, this term also encompasses the carriers mentioned in connection with the pharmaceutical composition as used in accordance with the present invention.

In accordance with the present invention, the term "foodstuff" encompasses all eatable and drinkable food and drinks. Accordingly, the microorganism, inactivated form, derivative, analog or fragment thereof may be included in a food or drink. These are, for example, gum, spray, beverage, candies, infant formula, ice cream, frozen dessert, sweet salad dressing, milk preparations, cheese, quark, lactose-free yogurt, acidified milk, coffee cream or whipped cream and the like.

Milk-based products are envisaged within the framework of the invention. Milk is however understood to mean that of animal origin, such as cow, goat, sheep, buffalo, zebra, horse, donkey, or camel, and the like. The milk may be in the native state, a reconstituted milk, a skimmed milk or a milk supplemented with compounds necessary for the growth of the bacteria or for the subsequent processing of fermented milk, such as fat, proteins of a yeast extract, peptone and/or a surfactant, for example. The term milk also applies to what is commonly called vegetable milk, that is to say extracts of plant material which have been treated or otherwise, such as leguminous plants (soya bean, chick pea, lentil and the like) or oilseeds (colza, soya bean, sesame, cotton and the like), which extract contains proteins in solution or in colloidal suspension, which are coagulable by chemical action, by acid fermentation and/or by heat. Finally, the word milk also denotes mixtures of animal milks and of vegetable milks.

Where the microorganism of this invention, inactivated form, or derivative or analog or fragment thereof are added to yogurt and the like having similar contents, it is generally sufficient to add the microorganism of this invention at a concentration of about $10^5$-$10^7$ cells/ml.

Such food drink or feed can be produced by a general method for producing foods and drinks or feeds, including adding the active ingredient to a raw or cooked material of the food, drink or feed. The food, drink or feed in accordance with the present invention can be molded and granulated in the same manner as generally used for foods, drinks or feeds. The molding and granulating method includes granulation methods such as fluid layer granulation, agitation granulation, extrusion granulation, rolling granulation, gas stream granulation, compaction molding granulation, cracking granulation, spray granulation, and injection granulation, coating methods such as pan coating, fluid layer coating, and dry coating, puff dry, excess steam method, foam mat method, expansion methods such as microwave incubation method, and extrusion methods with extrusion granulation machines and extruders.

The food, drink or feed of the present invention includes any food, drink or feed which comprises the microorganism of the invention, inactivated form, derivative or analog or fragment thereof as active ingredient. The active ingredient in the food, drink or feed is not specifically limited to any concentration as long as the resulting food, drink or feed can exert its activity of reducing oral malodour. The concentration of the active ingredient is preferably 0.001 to 100% by weight, more preferably 0.01 to 100 by weight and most preferably 0.1 to 100% by weight of the food, drink or feed comprising such active ingredient or with respect to the cell number those described herein.

Specific foods or drinks, to which the active ingredient is added, include, for example, juices, refreshing drinks, soups, teas, sour milk beverages, dairy products such as fermented milks, ices, butter, cheese, processed milk and skim milk, meat products such as ham, sausage, and hamburger, fish meat cake products, egg products such as seasoned egg rolls and egg curd, confectioneries such as cookie, jelly, snacks, and chewing gum, breads, noodles, pickles, smoked products, dried fishes and seasonings. The form of the food or drink includes, for example, powder foods, sheet-like foods, bottled foods, canned foods, retort foods, capsule foods, tablet foods and fluid foods.

The food or drink with according to the invention to be ingested by infants, are preferably nutritious compositions for infants. Such nutritious composition for infants includes modified milk prepared for infants, protein-decomposed milk, specific nutritionally modified milk or baby foods and foods prepared for toddlers. The form of the nutritious composition for infants includes but is not specifically limited to powder milks dried and pulverized and baby foods and also include general foods such as ice cream, fermented milk, and jelly for infantile ingestion.

The nutritious composition for infants in accordance with the present invention is principally composed of protein, lipid, saccharide, vitamins and/or minerals. In the nutritious composition, the active ingredient is blended with these components. The protein includes milk proteins such as skim milk, casein, cheese whey, whey protein concentrate and whey protein isolates and their fractions such as alpha s-casein, beta-casein, alpha-lactoalbumin and beta-lactoglobulin. Further, egg protein such as egg yolk protein, egg white protein, and ovalbumin, or soybean protein such as defatted soybean protein, separated soybean protein, and concentrated soybean protein can be used. Other than these, proteins such as wheat gluten, fish meat protein, cattle meat protein and collagen may also be used satisfactorily. Further, fractions of these proteins, peptides from the acid or enzyme treatment thereof, or free no acids maybe used satisfactorily as well. The free amino acids can serve as nitrogen sources and can additionally be used to give specific physiological actions. Such free amino acids include, for example, taurine, arginine, cysteine, cystine and glutamine. The lipid includes animal fats and oils such as milk fat, lard, beef fat and fish oil, vegetable oils such as soybean oil, rapeseed oil, corn oil, coconut oil, palm oil, palm kernel oil, safflower oil, perilla oil, linseed oil, evening primrose oil, medium chain fatty acid triglyceride, and cotton seed oil, bacterially generated fats and oils, and fractionated oils thereof, hydrogenated oils thereof, and ester exchange oils thereof. The amount of lipid to be blended varies depending on the use.

The saccharide includes, for example, one or more of starch, soluble polysaccharides, dextrin, monosaccharides such as sucrose, lactose as described herein, maltose, glucose, and fructose and other oligosaccharides. The total amount of such saccharide is preferably 40 to 80% by weight to the total solid in the nutritious composition. Further, artificial sweeteners such as aspartame may be used satisfactorily. The amount of an artificial sweetener is appropriately 0.05 to 1.0% by weight per the total solid in the nutritious composition.

The vitamins include, but are not limited to, lycopene as an essential component and additionally include, for example, vitamins such as vitamin A, vitamin B group, vitamins C, D, and E and vitamin K group, folic acid, pantothenic acid, niootinamide, carnitine, choline, inositol and biotin as long as such vitamins can be administered to infants. Such vitamins are preferably from 10 mg to 5 g by weight per the total solid in the nutritious composition for infants.

Further, the minerals include calcium, magnesium, potassium, sodium, iron, copper, zinc, phosphorus, chlorine, manganese, selenium and iodine. Such minerals are preferably from 1 mg to 5 g by weight per the total solid in the nutritious composition for infants.

Other than those components described above, the nutritious composition for infants in accordance with the present invention may be blended with any component desirably blended in nutritious compositions, for example, dietary fiber, nucleotides, nucleic acids, flavors, and colorants.

The food or drink in accordance with the present invention can be used as a health food or drink or a functional food or drink to prevent and/or treat oral malodour.

When the food or drink according to the present invention is ingested, the amount to be ingested is not specifically limited. The amount to be ingested is generally 0.1 to 50 g, preferably 0.5 g to 20 g daily, based on the total amount of active ingredient. The food or drink is continuously ingested at this amount for a period from a single day up to 5 years, preferably from 2 weeks to one year. Herein, the amount ingested can be adjusted to an appropriate range depending on the severity of the symptom of the individual ingesting the food or drink, the age and body weight thereof, and the like.

The feed according to the present invention maybe any feed comprising the active ingredient. The feed includes, for example, pet feeds for dogs, cats and rats, cattle feeds for cows and pigs, chicken feeds for chicken and turkeys, and fish cultivation feeds for porgy and yellowtail.

The feed can be produced by appropriately blending the active ingredient as described herein above in a raw feed material including, for example, cereals, brans, oil-seed meals, animal-derived raw feed materials, other raw feed materials and purified products.

The cereals include, for example, mile, wheat, barley, oats, rye, brown rice, buckwheat, fox-tail millet, Chinese millet, Deccan grass, corn, and soybean.

The brans include, far example, rice bran, defatted rice bran, bran, lowest-grade flour, wheat germ, barley bran, screening pellet, corn bran, and corn germ.

The oil-seed meals include, for example, soybean meal, soybean powder, linseed meal, cottonseed meal, peanut meal, safflower meal, coconut meal, palm meal, sesame meal, sunflower meal, rapeseed meal, kapok seed meal and mustard meal.

The animal-derived raw feed materials include, for example, fish powders, import meal, whole meal, and coast meal, fish soluble, meat powder, meat and bone powder, blood powder, decomposed hair, bone powder, byproducts from butchery, feather meal, silkworm pupa, skim milk, casein, dry whey and krill.

Other raw feed materials include, for example, plant stems and leaves such as alfalfa, hey cube, alfalfa leaf meal, and locust leaf powder, byproducts from corn processing industries, such as corn gluten meal, corn gluten feed and corn steep liquor, starch, sugar, yeast, byproducts from fermentation industry such as beer residue, malt root, liquor residue and soy sauce residue, and agricultural byproducts such as citrus processed residue, soybean curd residue, coffee residue, and cocoa residue, cassava, horse bean, guar meal, seaweed, spirulina and chiorella.

The purified products include, for example, proteins such as casein and albumin, amino acids, starch, cellulose, saccharides such as sucrose and glucose, minerals and vitamins.

In case of providing to animals the feed according to the present invention, the amount of the feed to be ingested is not specifically limited but is preferably, for example, 0.1 mg to 50 g per I kg body weight per day, preferably 0.5 mg to 20 g per 1 kg body weight per day, based on the amount of the active ingredient. The feed is continuously ingested at this amount for a period from a single day up to 5 years, preferably from 2 weeks to one year. Again, the amount ingested can be adjusted to an appropriate range depending on the species, age and body weight of the animal ingesting the feed, and the like.

In a further embodiment, the present invention relates to an additive for foods, drinks or feeds comprising a microorganism according to the present invention, an inactive form thereof, mutant, derivative, analog or fragment as well as to the use of a microorganism according to the present invention an inactive form thereof, mutant, derivative, analog or fragment for the preparation of a composition for the treatment and/or prophylaxis of oral malodour and/or halitosis, wherein the composition is an additive for foods, drinks or feeds. Preferably, the additive for foods or drinks includes the additive for nutritious compositions for infants.

The additive for foods can be produced by a general method for producing additives for foods, drinks or feeds. If necessary, additives for general use in foods, drinks or feeds, for example, additives described in Food Additive Handbook (The Japan Food Additives Association; issued on Jan. 6, 1997) may be added satisfactorily, including sweeteners, colorants, preservatives, thickeners and stabilizers, anti-oxidants, color fixing agents, bleaches, antiseptics, gum base, bitters, enzymes, brightening agents, acidifier, seasonings, emulsifiers, enhancers, agents for manufacture, flavors, and spice extracts. Further, conventional saccharides, starch, inorganic materials, plant powders, excipients, disintegrators, lubricants, binders, surfactants, and plasticizers mentioned previously for pharmaceutical tablets may be added satisfactorily.

The additives include the following additives.

The sweeteners include aspartame, licorice, stevia, xylose and rakanka (Momordica grosvenori fruit). The colorants include carotenoid and turmeric oleoresin, flavonold, caramel color, spirulina color, chlorophyll, purple sweet potato color, purple yam color, perilla color, and blueberry color.

The preservatives include, for example, sodium sulfite, benzoates, benzoin extract, sorbates, and propionates. The thickeners and stabilizers include, for example, gums such as gum arable and xanthan gum, alginates, chitin, chitosan, aloe extract, guar gum, hydroxypropyl cellulose, sodium casein, corn starch, carboxymethyl cellulose, gelatin, agar, dextrin, methyl cellulose, polyvinyl alcohol, microfiber cellulose, microcrystalline cellulose, seaweed cellulose, sodium polyacrylate, sodium polyphosphate, carrageenan or yeast cell wall.

The anti-oxidants include, for example, vitamin C group, sodium ethylenediaminetetraacetate, calcium ethylenediaminetetraacetate, erythorbic acid, oryzanol, catechin, quercetin, clove extract, enzyme-treated rutin, apple extract, sesame seed extract, dibutylhydroxytoluene, fennel extract, horseradish extract, water celery extract, tea extract, tocopherols, rapeseed extract, coffee bean extract, sunflower seed extract, ferulio acid, butylhydroxyanisole, blueberry leaf extract. propolis extract, pepper extract, garden balsam extract, gallic acid, eucalyptus extract, and rosemary extract.

The color fixing agents include, for example, sodium nitrite. The bleaches include, for example, sodium sulfite.

The antiseptics include, for example, o-phenyl phenol. The gum base includes, for example, acetylricinoleate methyl, urushi wax, ester gum, elemi resin, urucury wax, kaurigum, carnaubawax, glycerin fatty acid ester, spermaceti wax, copaibabalsam, copal resin, rubber, rice bran wax, cane wax, shellac, jelutong, sucrose fatty acid ester, depolymerized natural rubber, paraffin wax, fir balsam, propylene glycol fatty acid ester, powdered pulp, powdered rice hulls, jojoba oil, polyisobutylene, polybutene, microcrystalline wax, mastic gum, bees wax and calcium phosphate.

The bitters include, for example, iso-alpha-bitter acid, caffeine, kawaratake (Coriolus versieolor) extract, redbark cinchona extract, Phellodendron bark extract, gentian root extract, spice extracts, enzymatically modified naringin, Jamaica cassia extract, theabromine, naringin, cassia extract, absinth extract, isodonis extract, olive tea, bitter orange (Citrus aurantium) extract, hop extract and wormwood extract.

The enzymes include, for example, amylase, trypsin or rennet.

The brightening agents include, for example, urushi wax and japan wax. The acidifier include, for example, adipic acid, itacania acid, citric acids, succinic acids, sodium acetate, tartaric acids, carbon dioxide, lactic acid, phytic acid, fumario acid, malic acid and phosphoric acid. The seasonings include, for example, amino acids such as asparagine, aspartic acid, glutamic acid, glutamine, alanine, isoleucine, glycine, serine, cystine, tyrosine, leucine, and praline, nucleic acids such as sodium inosinate, sodium uridinate, sodium guanylate, sodium cytidylate, calcium ribonucleotide and sodium ribonucleotide, organic acids such as citric acid and succinic acid, potassium chloride, sodium chloride-decreased brine, crude potassium chloride, whey salt, tripotassium phosphate, dipotassium hydrogen phosphate, potassium dihydrogen phosphate, disodium hydrogen phosphate, sodium dihydrogen phosphate, trisodium phosphate and chlorella extract.

The enhancers include, for example, zinc salts, vitamin C group, various amino acids, 5-adenylic acid, iron chloride, hesperidin, various calcined calcium, various non-calcined calcium, dibenzoylthiamine, calcium hydroxide, calcium carbonate, thiamine hydrochloride salt, Dunallella. Oarotene, tocopherol, nicotinic acid, carrot carotene, palm oil carotene, calcium pantothenate, vitamin A, hydroxyproline, calcium dihydrogen pyrophosphate, ferrous pyrophosphate, ferric pyrophosphate, ferritin, heme iron, menaquinone, folic acid and riboflavine.

The agents for manufacture include, for example, processing auxiliaries such as acetone and ion exchange resin. The flavors include, for example, vanilla essence and the spice extracts include, for example, capsicum extract.

These various additives can be added to the active ingredient, taking into consideration the mode of administration, in accordance with the present invention.

The composition according to the present invention encompasses a microorganism according to the invention. It is envisaged that the compositions comprises the microorganism in the form of a probiotic microorganism. Namely, in addition to the probiotic effect, the above mentioned probiotic microorganism belonging to the group of lactic acid bacteria is useful for treating and/or preventing oral malodour and/or halitosis. The amount of said probiotic microorganism is high enough to significantly positively modify the condition to be treated, preferably oral malodour, but low enough to avoid serious side effects (at a reasonable benefit/risk ratio), within the scope of sound medical judgment. An effective amount of said probiotic microorganism will vary with the particular goal to be achieved, the age and physical condition of the patient being treated, the severity of the underlying disease, the duration of treatment, the nature of concurrent therapy and the specific microorganism employed. The effective amount of said probiotic microorganism will thus be the minimum amount which will provide the desired effect. The presence of, for example, $1\times10^9$ bacteria, as viable or non-viable whole cells, in 0.05 ml solution of phosphate buffered saline solution, or in 0.05 ml of suspension of agar, or the dry weight equivalent of cell wall fragments, is effective when administered in quantities of from about 0.05 ml to about 20 ml.

A decisive practical advantage is that the probiotic organism may be administered in a convenient manner such as by the oral route. Depending on the route of administration, the active ingredients which comprise said probiotic organisms may be required to be coated in a material to protect said organisms from the action of enzymes, acids and other natural conditions which may inactivate said organisms. In order to administer probiotic organisms by other than parenteral administration, they should be coated by, or administered with, a material to prevent inactivation. For example, probiotic organisms may be co-administered with enzyme inhibitors or in liposomes. Enzyme inhibitors include pancreatic trypsin inhibitor, diisopropylfluorophosphate (DFP) and trasylol. Liposomes include water-in-oil-in-water P40 emulsions as well as conventional and specifically designed liposomes which transport lactobacilli or their by-products to the urogenital surface. Dispersions can also be prepared, for example, in glycerol, liquid polyethylene glycols, and mixtures thereof, and in oils. Generally, dispersions are prepared by incorporating the various sterilized probiotic organisms into a sterile vehicle which contains the basic dispersion medium and the required other ingredients from those enumerated above. In the case of sterile powders for the preparation of sterile injectable solutions, the preferred methods of preparation are vacuum-drying and the freeze-drying technique which yield a powder of the active ingredient plus any additional desired ingredient from previously sterile-filtered solution thereof. Additional preferred methods of preparation include but are not limited to lyophilization and heat-drying.

The composition also encompasses products intended to be administered orally, or buccal, which comprise an acceptable pharmaceutical carrier as described herein to which, or onto which, cells of the above mentioned microorganism belonging to the group of lactic acid bacteria is added in fresh, concentrated or dried form, for example. Of course, also an inactivated form, derivative or analog or fragment of said microorganism can be added or any combination of said microorganism, derivative and/or analog and/or fragment thereof which are disclosed herein. These products may be provided in the form of an ingestible suspension, a gel, a diffuser, a capsule, a hard gelatin capsule, a syrup, or in any other galenic form known to persons skilled in the art.

When the probiotic organisms are suitably protected as described above, the active compound may be orally administered, for example, with an inert diluent or with an assimilable edible carrier, or it may be enclosed in hard or soft shell gelatin capsule, or it may be compressed into tablets designed to pass through the stomach (i.e., enteric coated), or it may be incorporated directly with the food of the diet. For oral therapeutic administration, the probiotic organisms may be incorporated with excipients and used in the form of ingestible tablets, buccal tablets, troches, capsules, elixirs, suspensions, syrups, wafers, and the like. Compositions or preparations according to the present invention are prepared so that an oral dosage unit form contains, for example, about $1 \times 10^9$ viable or non-viable e.g., lactobacilli per ml. The probiotic organism is compounded for convenient and effective administration in effective amounts with a suitable pharmaceutically or food acceptable carrier in dosage unit form as hereinbefore disclosed. A unit dosage form can, for example, contain the principal active compound in an amount approximating $10^9$ viable or non-viable, e.g., lactobacilli, per ml. In the case of compositions containing supplementary ingredients such as prebiotics, the dosages are determined by reference to the usual dose and manner of administration of the said ingredients.

In a further embodiment, the present invention relates to a method of prophylaxis and/or treatment of oral malodour and/or halitosis. Preferably the method of prophylaxis and/or treatment comprises administering to a subject a microorganism according to the present invention or an inactivated form, or a mutant, derivative, analog or fragment of said microorganism as described herein above.

Preferably, the subject to be treated is an animal. More preferably, the animal is a mammal, even more preferably the mammal is a pet mammal. In a preferred embodiment, the pet is a dog, a cat, a hamster, a monkey, a rat or a mouse. In another preferred embodiment the animal is cattle, a horse, a swine, a donkey, a sheep or a goat. In another preferred embodiment the mammal is a human being.

The administration of a microorganism according to the invention in the context of the method of treatment and/or prophylaxis of the present invention may be carried out in any suitable form known to the person skilled in the art. Preferably, the administration encompasses the use and application of compositions as described herein above, which may optionally contain, for example, pharmaceutical or cosmetic carriers or excipients as described herein above. The dosage and time course of the administration may be established according any suitable information known to the person skilled in the art. Preferably, said dosage and time course may be established as described herein above.

The invention is illustrated by FIGS. 1 to 7 as described in the following:

Figure 1:
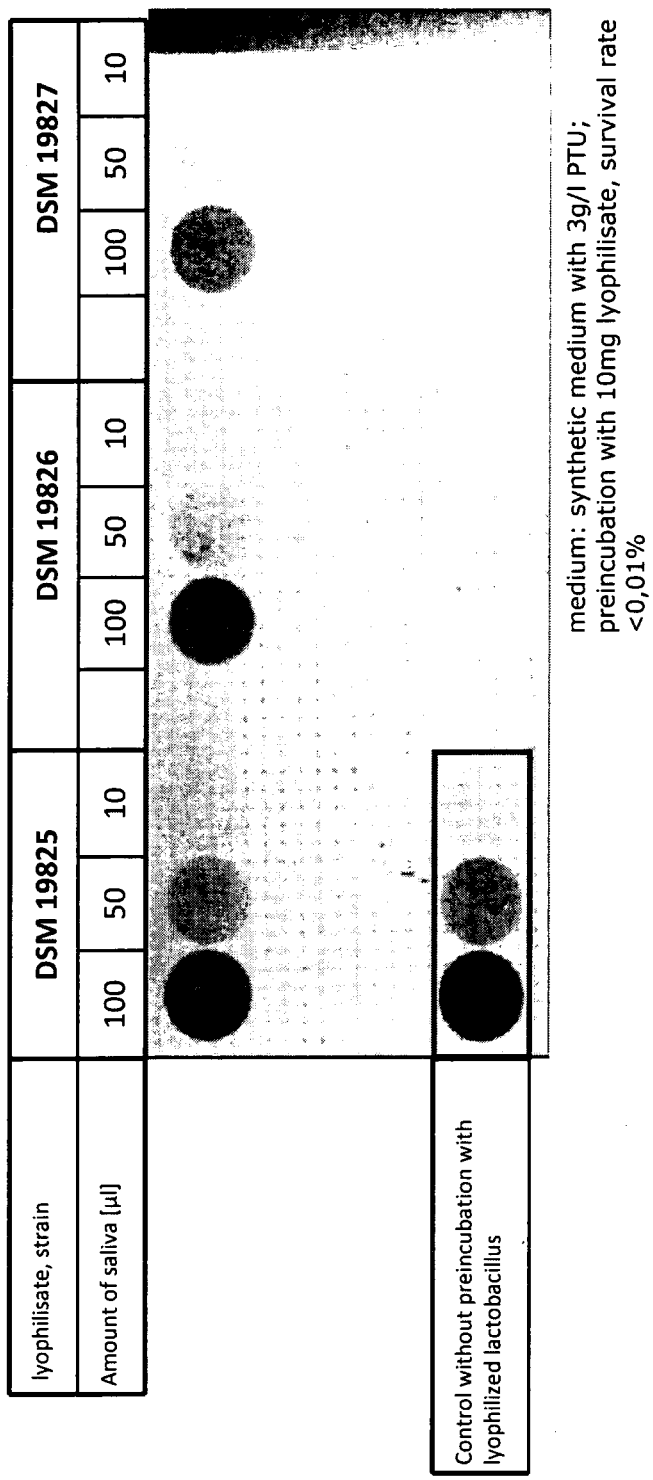
FIG. 1 shows the results of an experiment analyzing the influence of the reduction in peptide concentration by lactobacilli on $H_2S$ production by gram negative anaerobic bacteria present in saliva.

A better understanding of the present invention and of its many advantages will be had from the following examples, offered for illustrative purposes only, and are not intended to limit the scope of the present invention in any way.

EXAMPLE 1

Media

TSY-Medium:

| | |
|---|---|
| TSY-mixture (Difco, USA) | 30 g/l |
| Yeast extract (Deutsche Hefewerke, Germany) | 3 g/l |

MRS Light-Medium:

| | |
|---|---|
| Peptone Trypticase: | 1.0 g/l |
| Yeast Extract: | 0.5 g/l |
| di-Ammonium hydrogen citrate: | 0.2 g/l |
| Sodium-Acetate: | 0.5 g/l |
| $MgSO_4$-Heptahydrate: | 0.050 g/l |
| $MnSO_4$-Monohydrate: | 0.025 g/l |
| D-Glucose-Monohydrate: | 1 g/l |
| $K_2HPO_4$: | 0.2 g/l |
| Oleic Acid: | 0.1% (w/v) |

Synthetic Medium:

| | |
|---|---|
| Guanin: | 0.1 g/l |
| Cytosine: | 0.1 g/l |
| Thymidine: | 0.1 g/l |
| 2'-Deoxyadenosine: | 0.1 g/l |
| 2'-Deoxyuridine: | 0.1 g/l |
| $K_2HPO_4$: | 2 g/l |
| Sodium-Acetate: | 5 g/l |
| $MgSO_4$-Heptahydrate: | 0.1 g/l |
| di-Ammonium hydrogen citrate: | 2 g/l |
| $CaCl_2$-dihydrate: | 0.5 g/l |
| Oleic Acid: | 0.1% (w/v) |
| Cyanocobalamine: | 0.02 mg/l |
| Riboflavine: | 10 mg/l |
| Folic Acid: | 0.2 mg/l |
| Pyridoxal-5-phosphate-monohydrate: | 10 mg/l |
| 4-Aminobenzoic acid: | 0.2 mg/l |
| D (+)-Biotin: | 1 mg/l |
| Ascorbic Acid: | 500 mg/l |
| Nicotinic Acid: | 10 mg/l |
| Ca-Panthotenate: | 10 mg/l |
| Thiamine: | 1 mg/l |
| Cobalt(II)-Nitrat-Hexahydrate: | 500 mg/l |
| $MnSO_4$-Monohydrate: | 20 mg/l |
| $MgSO_4$-Heptahydrate: | 500 mg/l |
| $Na_2MoO_4$: | 0.04 mg/l |
| PTU-Extract (Ohly, Deutsche Hefewerke Germany): | 15 g/l (or as stated elsewhere) |
| D-Glucose-Monohydrate: | 10 g/l |

FAB Medium:

| | |
|---|---|
| Peptone mixture | 15.0 g/l |
| Yeast Extract | 10.0 g/l |
| Sodium thioglycollate | 0.5 g/l |
| Sodium chloride | 2.5 g/l |
| Agar No. 1 | 0.75 g/l |
| L-Cysteine HCl | 0.5 g/l |
| Resazurin | 0.001 g/l |
| Sodium bicarbonate | 0.4 g/l |
| Haemin | 0.005 g/l |
| Vitamin K | 0.0005 g/l |

Storage and Growth

Storage and growth of strains can occur according to ordinary procedures. For example, strains can be stored as frozen stocks at −80° C. 1 ml of a culture can be grown to stationary phase (OD600/mL 4-8) in MRS-Medium and mixed with 500 µl of a sterile 50% glycerine solution and frozen.

Cultures of *S. salivarius* were grown in TSY-media to stationary phase ($OD_{600}$/ml 1-2) and treated as mentioned above. The *S. salvarius* strain preferably used in the experiments was *S. salivarius* DSM 20560 (Andrews and Horder, 1906).

Cultivation of *S. salivarius* (DSM 20560) as well as isolates was done anaerobically in 6-Well-Plates with 8 ml of TSY-Medium over night at 37° C.

Lactobacilli (DSM 19825, 19826, 19827) were anaerobically cultivated in 150 µl of synthetic medium in 96-Well-Plates for 24 hours at 37° C.

The mixture of lactobacilli and *S. salivarius* was done in cell count ratios of 1:100 (*lactobacillus:S. salivarius*) in ½ TSY medium. This was done in 96-well-plates.

The culture suspension was incubated for 12 h in a BioTek PowerWave microplate spectrophotometer at 37° C.

As a control, unconsumed ½ TSY-Medium or MRS light-Medium was used instead of lactobacilli culture.

Growth stimulation of *S. salivarius* was visible by comparing the maximum optical density ($OD_{600,\ max}$) or the maximum growth rate ($V_{max}$) with and without lactobacilli after 10 hours of incubation ($OD_{600,\ max}$) or during exponential growth ($V_{max}$).

Stimulation is defined as an increased maximum optical density ($OD_{600,\ max}$) or maximum growth rate ($V_{max}$) by at least 10%.

EXAMPLE 2

Taxonomic Classification of Strains

The taxonomic classification of the strains was done according to their carbohydrate fermentation pattern. This was determined using the API 50 CH (bioMerieux, France) system and analyzed using APILAB PLUS software version 3.3.3 (bioMerieux, France).

EXAMPLE 3

Test on Growth Stimulation of *Streptococcus Mutants* with Lactobacilli Supernatant The bacteria were cultivated as in Example 1. The supernatant of lactobacilli (in particular DSM 19826) was obtained by centrifugation at 4000×g for 15min. The mixture of the lactobacilli supernatant with *S. salivarius* was done in volumetric ratios of 2:1 to 4:1 (*S. salivarius*:lactobacilli-supernatant) in ½ TSY-Medium. This was done in 96-Well-Plates. The culture suspension was incubated for 12 h in a BioTek PowerWave microplate spectrophotometer at 37° C. As a control, unconsumed ½ TSY-Medium or MRS light-Medium was used instead of lactobacilli supernatant.

Figure 2:
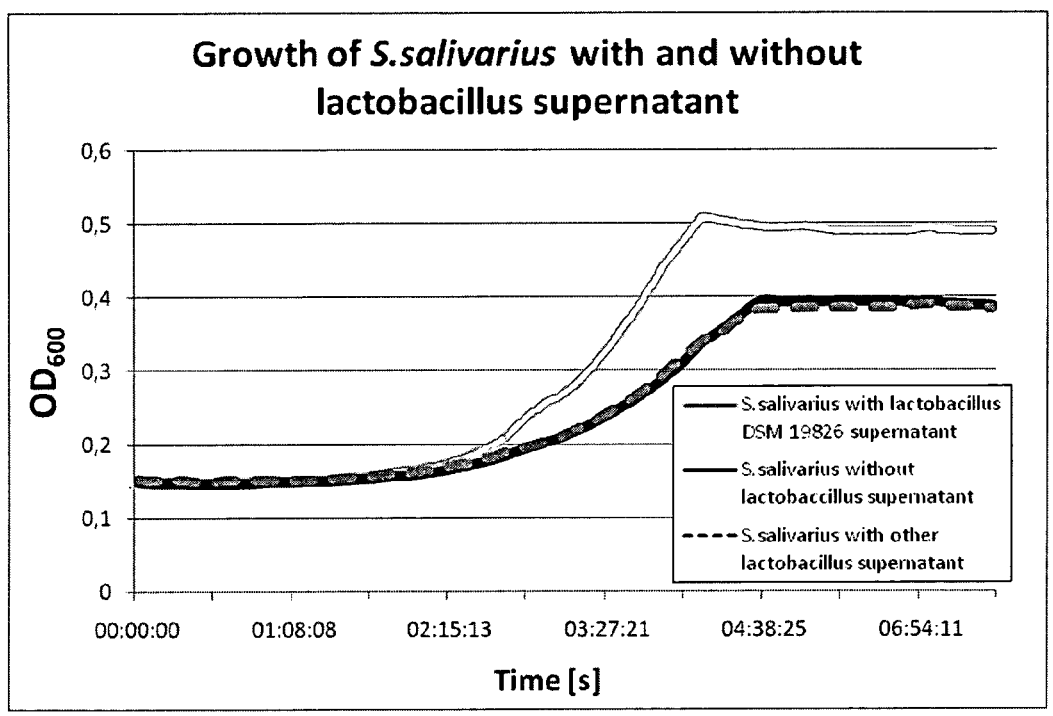
FIG. 2 shows the results of an experiment analyzing the influence of *lactobacillus* supernatants on the growth of *S. salivarius* as described in Example 3.

Growth stimulation was assayed as in Example 1. A successful stimulation of the growth of *S. salivarius* with supernatants of the lactobacilli could be observed. These results are shown in FIG. 2.

EXAMPLE 4

Non-stimulation of Oral Pathogen Member of the Oral Flora *S. Mutans*

The *S. salivarius* cultures were grown as in Example 1. *Streptococcus mutans* (DSM 20253) was grown in 5 ml TSY Medium in closed 15 ml Falcon tubes over night. The oral bacteria were mixed in a volumetric ratio of 2:1 with lactobacilli supernatant and growth was assayed as in Example 1. As a control, oral bacteria were cultivated with unconsumed ½ TSY-Medium instead of lactobacilli supernatant.

No growth stimulation of the oral pathogen *S. mutans* by the lactobacilli could be observed.

Moreover, non-stimulation of *S. mutans* growth can be assayed by the following assay:

Lactobacilli (e. g. DSM 19825, 19826, 19827) are anaerobically cultivated in 150 µl of synthetic medium in 96-well-plates for 24 hours at 37° C. *Streptococcus mutans* (DSM 20253) is grown under anaerobic conditions in 5 ml TSY medium in closed 15 ml Falcon tubes overnight at 37° C. The mixture of lactobacilli and *S. mutans* is done in cell count ratios of 1:100 (*lactobacillus:S. mutans*) in ½ TSY medium. This is done in 96-well-plates. The culture suspension is aerobically incubated for 12 h in a BioTek PowerWave microplate spectrophotometer at 37° C. As a control, unconsumed ½ TSY medium is used instead of lactobacilli culture.

EXAMPLE 5

Non-Stimulation of Oral Pathogen Member of the Oral Flora *P. Gingivalis*

The *S. salivarius* cultures were grown as in Example 1. *Porphyromonas gingivalis* (DSM 20709) was grown anaerobically in 5 ml FAB-medium in closed 15 ml Falcon tubes at 37° C. overnight. *P. gingivalis* was mixed in a volumetric ration of 2:1 with lactobacilli supernatant (from DSM 19826) and cultivated anaerobically in 96-well-plates. As a control, *P. gingivalis* was cultivated with unconsumed FAB-medium instead of lactobacilli supernatant.

Figure 3:
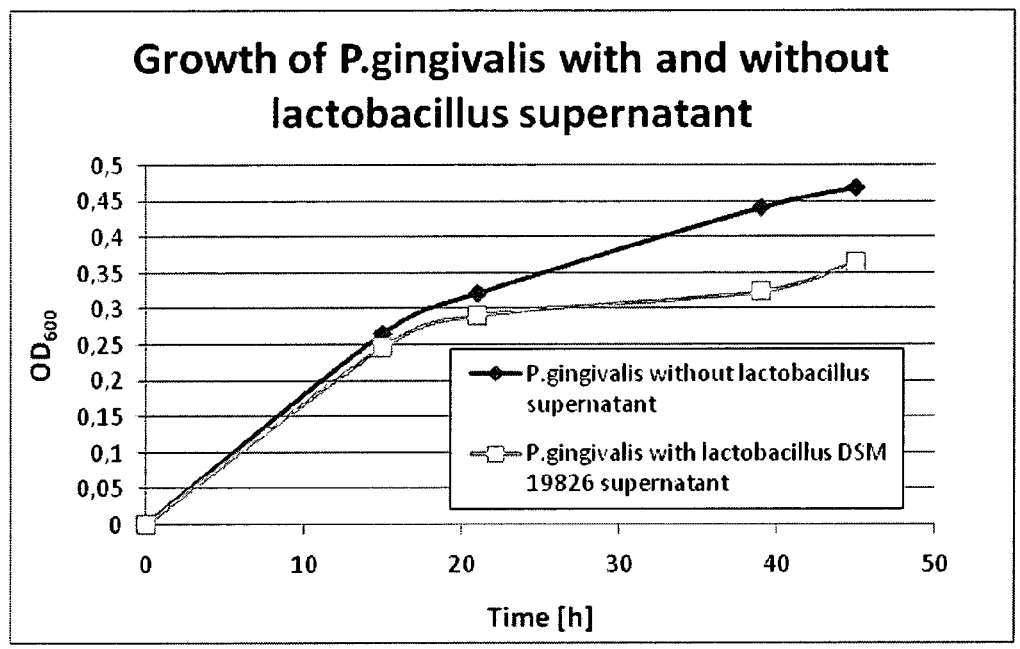
FIG. 3 shows the results of an experiment analyzing the influence of *lactobacillus* on the growth of *P. gingivalis* as described in Example 5.

No growth stimulation of the oral pathogen *P. gingivalis* by the lactobacilli was observed. The results are shown in FIG. 3.

Moreover, non-stimulation of *P. gingivalis* growth can be assayed by the following assay:

Lactobacilli (e. g. DSM 19825, 19826, 19827) are anaerobically cultivated in 150 µl of synthetic medium in 96-well-plates for 24 hours at 37° C. *Porphyromonas gingivalis* (DSM 20709) is grown anaerobically in 5 ml FAB medium in closed 15 ml Falcon tubes at 37° C. overnight. The mixture of lactobacilli and *P. gingivalis* is done in cell count ratios of 1:100 (*lactobacillus:P. gingivalis*) in FAB medium. This is done in 96-well-plates. The culture suspension is aerobically incubated for 45 h in a Whitley DG250 anaerobic workstation (Meintrup-DWS, Germany) at 37° C. As a control, unconsumed FAB medium is used instead of lactobacilli culture.

EXAMPLE 6

Temperature Resistance of the Stimulating Capacity of the Lactobacilli

The bacteria were grown as in Example 1. The lactobacilli supernatants (of DSM 19827) were incubated at 80° C. for 10 min in an incubator. After cooling of the supernatant to room temperature, the lactobacilli supernatant was mixed in a volumetric ratio of 1:2 with grown *S. salivarius* cultures and stimulation was assayed as in Example 1 including the control experiments.

Figure 4:
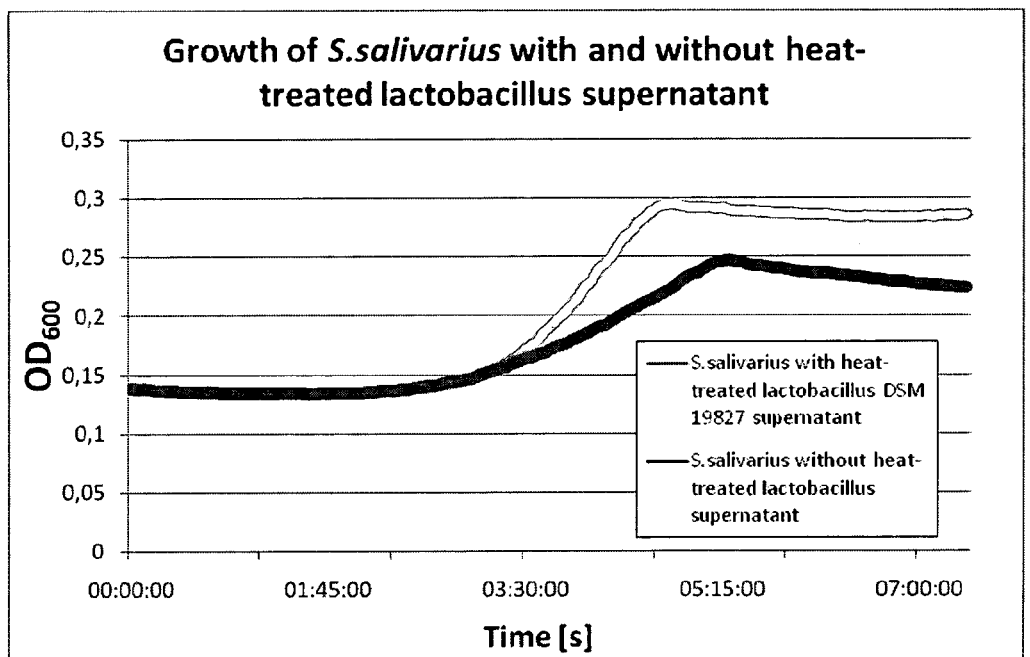
FIG. 4 shows the results of an experiment analyzing the influence of heat-treated *lactobacillus* supernatant on the growth of *S. salivarius* as described in Example 6.

(Stimulation was assayed as well using the oral pathogen bacteria as outlined in Examples 4 and 5. It was demonstrated that the non-stimulating behaviour of the lactobacilli towards the oral-pathogen bacteria is not influenced by heat treatment.) No influence by heat treatment on stimulatory activity towards *S. salivarius* could be observed. The results are shown in FIG. 4.

EXAMPLE 7

Sensitivity of the Stimulation to Lyophilisation

*S. salivarius* was grown as in Example 1. Lactobacilli were cultivated anaerobically in 50 ml synthetic media in closed 100 ml bottles (Schott, Germany) overnight at 37° C. Lactobacilli supernatant was obtained by centrifugation at 4000×g for 15 min. 20 ml of supernatant were froze to −80° C. and lyophilized under vacuum for 16 h. The lyophilized supernatant was resuspended in 20 ml of $H_2O$. The resuspended supernatant was mixed with *S. salivarius* culture in a ration of 2:1 (*S. salivarius*:resuspended supernatant) in ½ TSY medium in 96 well plates. Growth stimulation was assayed as in Example 1 including the control experiments.

The stimulatory activity was not decreased by lyophilisation.

EXAMPLE 8

Reduction of Peptide Concentration by the Lactobacilli

Lactobacilli (DSM 19827) were cultivated as in Example 1. The main culture was cultivated in synthetic medium containing 15g/l of peptides (PTU-extract). The medium was inoculated with 10 µl of culture suspension and anaerobically cultivated at 37° C. for 24 h. Then the peptide concentration was determined and it turned out that it has decreased at least by 20% after 24 h.

Figure 5:
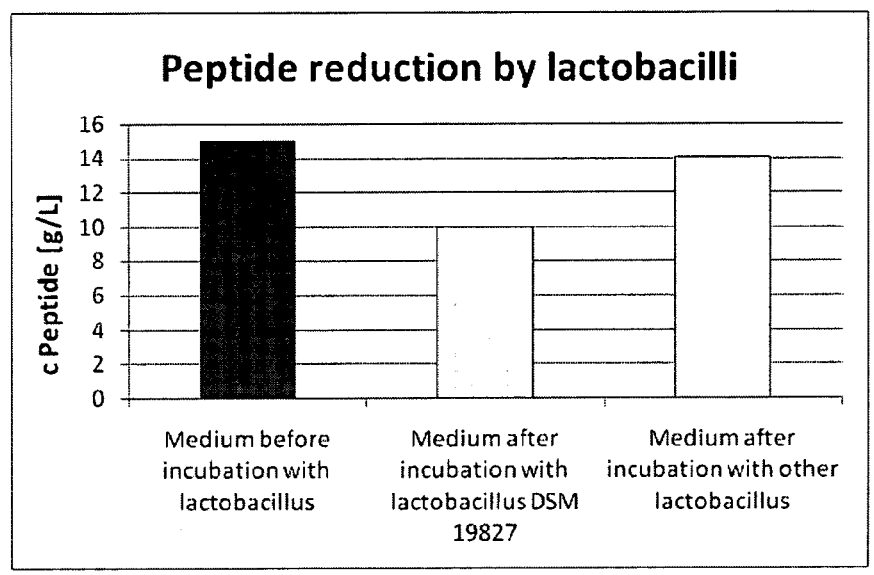
FIG. 5 shows the results of an experiment analyzing the reduction of the peptide concentration by *lactobacillus* according to the invention.

The results showed an effective reduction of the peptide concentration by the growing lactobacilli and are illustrated by FIG. 5.

EXAMPLE 9

Sensitivity of the Reduction of Peptide Concentration to Lyophilisation

Lactobacilli (DSM 19827) were cultivated in 100 ml of synthetic medium at 37° C. for 24 h. The whole culture was centrifuged at 4000×g for 15 min and resuspended in 20 ml of $H_2O$. 20 ml of resuspended lactobacilli were froze to −80° C. and lyophilised under vacuum for 16 h.

For the peptide uptake assay, 10 mg of lyophilised lactobacilli were resuspended in $H_2O$ and centrifuged at 4000×g for 10 min. 1 ml of synthetic medium containing 7 g/l peptides was added to the pellet and after 5 min of incubation at 37° C., the cells were removed by centrifugation. The peptide concentration in the supernatant was determined. The peptide concentration in the medium after cell removal was reduced to 2 g/l. This corresponds to an uptake of 0.5 mg of peptide/ mg of lyophilized lactobacilli.

Figure 6:
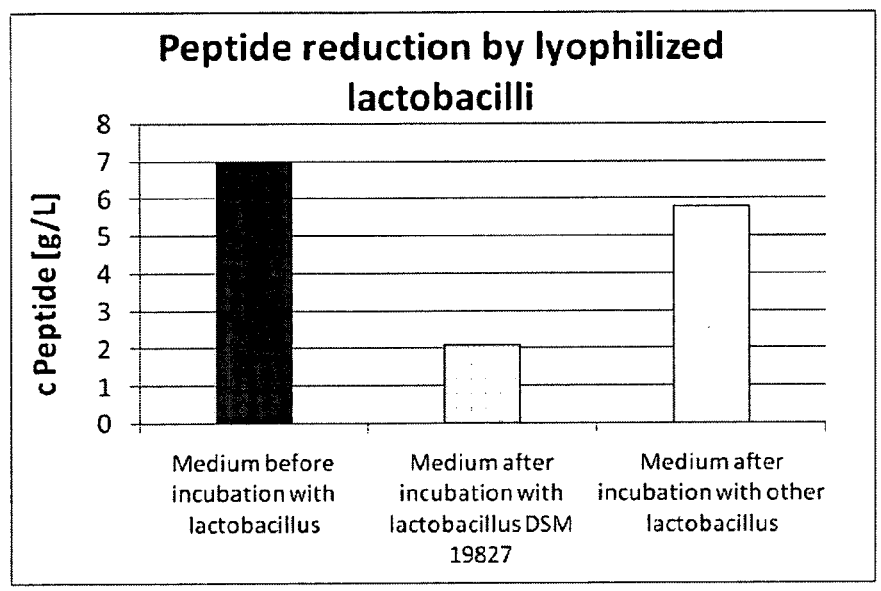
FIG. 6 shows the results of an experiment analyzing the reduction of the peptide concentration by lyophilized lactobacilli according to the invention.
Figure 7:
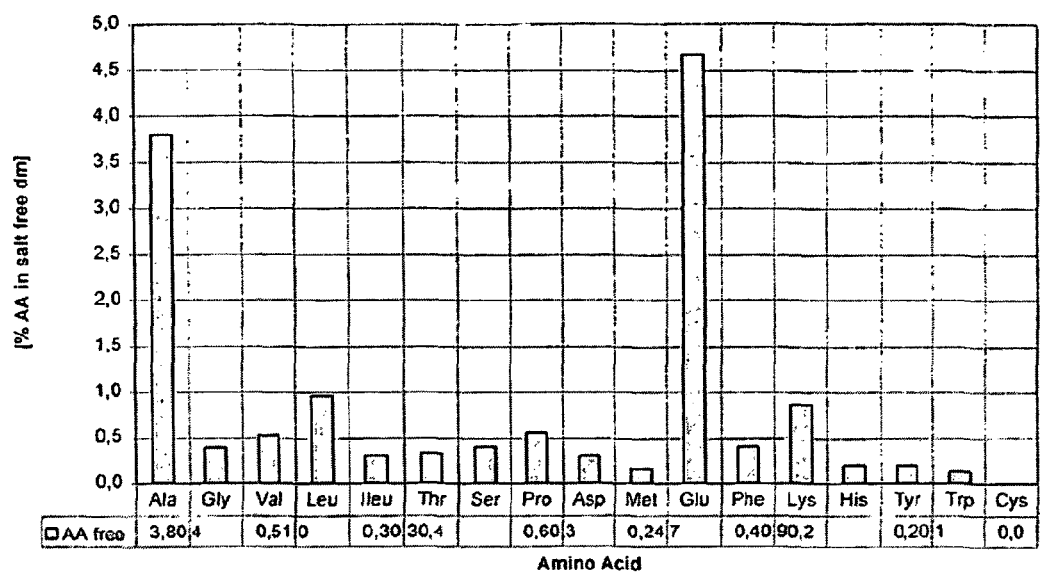
FIG. 7 shows a typical amino acid profile of PTU extract.

These results show an effective reduction in peptide concentration by the lactobacilli in a lyophilised state as illustrated in FIG. 6.

EXAMPLE 10

Influence of Reduction of Peptide Concentration by Lactobacilli on $H_2S$ Production by Gram Negative Anaerobic Bacteria Lactobacilli were cultivated and lyophilized as in Example 8. For the experiment, 10 mg of lyophilized lactobacilli were resuspended in $H_2O$ in a deep-well-plate and centrifuged at 4000×g for 10 min. 1 ml of synthetic medium containing 3 g/l of peptides was added to the pellet and after 5 min of incubation at 37° C., the cells were removed by centrifugation. The pH of the medium was not altered by the incubation.

The medium was then inoculated with 50pl of unsterile human saliva and anaerobically incubated for 6 h at 37° C. The deep-well-plate was covered with sterile filter paper impregnated with lead acetate. The production of hydrogen sulphide by microorganisms from the saliva was monitored by blackening of filter paper.

A reduced production of $H_2S$ in lactobacilli treated medium was observed by comparing the blackening to the control experiment without pre-incubation with lactobacilli.

These results show that a pre-incubation of medium with lactobacilli results in a decreased production of $H_2S$ during subsequent incubation of medium with microorganisms from the human saliva.

EXAMPLE 11

Lozenge Composition (I)

The lozenge composition is preferably prepared as is described in Example 4 on page 8 of DE-C2 36 45 147, wherein, in addition to the ingredients mentioned in said Example 4, the above mentioned microorganism belonging to the group of lactic acid bacteria is added in an amount of $10^2$ to $10^{12}$, preferably $10^3$ to $10^8$ cells per mg of the lozenge.

EXAMPLE 12

Lozenge Composition (II)

The lozenge composition is preferably prepared as is described in Example 5 on page 8 of DE-C2 36 45 147, wherein, in addition to the ingredients mentioned in said Example 5, the above mentioned microorganism belonging to the group of lactic acid bacteria is added in an amount of $10^2$ to $10^{12}$, preferably $10^3$ to $10^8$ cells per mg of the lozenge.

EXAMPLE 13

Dentifrice Composition

The dentifrice composition is preferably prepared as is described in Example 3 on page 8 of DE-C2 36 45 147, wherein, in addition to the ingredients mentioned in said Example 3, the above mentioned microorganism belonging to the group of lactic acid bacteria is added in an amount of $10^2$ to $10^{12}$, preferably $10^3$ to $10^8$ cells per mg of the dentifrice.

EXAMPLE 14

Chalk-based Dentifrice Composition

The chalk-based dentifrice composition is preferably prepared as is described in chapter 7.1.4.4 "Rezepturbeispiel" on page 205 of the textbook "Kosmetik", W. Umbach (editor), $2^{nd}$ edition, Thieme Verlag, 1995, wherein, in addition to the ingredients mentioned in said chapter on page 205, the above mentioned microorganism belonging to the group of lactic acid bacteria is added in an amount of $10^2$ to $10^{12}$, preferably $10^3$ to $10^8$ cells per mg of the chalk-based dentifrice.

EXAMPLE 15

Gel-Dentifrice on Basis of Silicic Acid/Sodium Fluoride

The gel-dentifrice on basis of silicic acid/sodium fluoride dentifrice composition is preferably prepared as is described in chapter 7.1.4.4 "Rezepturbeispiel" on page 205 of the textbook "Kosmetik", W. Umbach (editor), $2^{nd}$ edition, Thieme Verlag, 1995, wherein, in addition to the ingredients mentioned in said chapter on page 205, the above mentioned microorganism belonging to the group of lactic acid bacteria is added in an amount of $10^2$ to $10^{12}$, preferably $10^3$ to $10^8$ cells per mg of the gel-dentifrice on basis of silicic acid/sodium fluoride.

EXAMPLE 16

Dentifrice Composition Against Tartar

The dentifrice composition against tartar is preferably prepared as is described in chapter 7.1.4.4 "Rezepturbeispiel" on page 206 of the textbook "Kosmetik", W. Umbach (editor), $2^{nd}$ edition, Thieme Verlag, 1995, wherein, in addition to the ingredients mentioned in said chapter on page 206, the above mentioned microorganism belonging to the group of lactic acid bacteria is added in an amount of $10^2$ to $10^{12}$, preferably $10^3$ to $10^8$ cells per mg of the dentifrice against tartar.

EXAMPLE 17

Chewing Gum Composition

The chewing gum composition is preferably prepared as is described in Example 6 on page 9 of DE-C2 36 45 147, wherein, in addition to the ingredients mentioned in said Example 6, the above mentioned microorganism belonging to the group of lactic acid bacteria is added in an amount of $10^2$ to $10^{12}$, preferably $10^3$ to $10^8$ cells per mg of the chewing gum.

EXAMPLE 18

Concentrated Mouthwash Composition

The concentrated mouth wash composition is preferably prepared as is described in chapter 7.1.4.4 "Rezepturbeispiel" on page 206 of the textbook "Kosmetik", W. Umbach (editor), $2^{nd}$ edition, Thieme Verlag, 1995, wherein, in addition to the ingredients mentioned in said chapter on page 206, the above mentioned microorganism belonging to the group of lactic acid bacteria is added in an amount of $10^2$ to $10^{13}$, cells per ml of the concentrated mouthwash composition.

EXAMPLE 19

Film Preparation

Preparation of Films:
1. water phase
   heat water to 60° C.
   aspartame (sweetener) is added under stirring
   aspartame is dissolved completely
   a polymeric water-soluble film former, like, for example, Kollicoat IR (polyethylenglycol on polyvinylalcohol) or PVP (polyvinylpyrrolidon) or natural polymers such as alginates are added under stirring until they are dissolved
   after 10 min. the rest of the foam is removed
   the above mentioned microorganism belonging to the group of lactic acid bacteria in an amount of $10^2$ to $10^{12}$, preferably $10^3$ to $10^8$ cells per final aroma film is added after cooling down of the mixture; alternatively, the mutant or derivative of the above mentioned microorganism belonging to the group of lactic acid bacteria or an analog or fragment of the above mentioned microorganism belonging to the group of lactic acid bacteria can be added
2. oily phase
   menthol is dissolved in peppermint-oil
   polysorbat 80 is added to the peppermint-oil—menthol—mix under stirring
   this mixture is then added to propylene-glykole under stirring
   optional colorants (such as pigments, lakes) can be added
3. under stirring the oily phase is slowly mixed with the water phase
4. the thin films are mechanically generated using a cutting device Sample Formulations:

|  | formulation I weight [g] | composition in film [%] | formulation II weight [g] | composition in film [%] |
|---|---|---|---|---|
| Phase I | | | | |
| aspartame | 0.7 | 1.4 | 0.7 | 1.8 |
| Kollicoat IR | 35.0 | 68.5 | 25.0 | 65.8 |
| ascorbic acid | — | — | 1.0 | 2.6 |
| cherry flavour | | | 6.0 | 15.8 |
| water demin. | 85.0 | — | 80.0 | |
| Phase II | | | | |
| menthol | 1.4 | 2.7 | — | |
| peppermint oil | 5.6 | 11.0 | — | |
| polysorbat 80 | 0.7 | 1.4 | — | |
| propylene glykol | 7.0 | 13.7 | 5.0 | 13.2 |
| green lake | 0.7 | 1.4 | — | |
| azorubin lake | — | — | 0.3 | 0.8 |
| sum | 136.1 | 100.0 | 118.0 | 100.0 |
| solid content | 51.1 | | 38.0 | |

Other embodiments and uses of the invention will be apparent to those skilled in the art from consideration of the specification and practice of the invention disclosed herein. All references cited herein, for any reason, including all publications, all U.S: and foreign patents and all U.S. and foreign patent applications, are specifically and entirely incorporated by reference for all purposes. It is intended that the specification and examples be considered exemplary only with the true scope and spirit of the invention indicated by the following claims.

The invention claimed is:

1. An isolated microorganism of the genus *Lactobacillus* capable of reducing peptide concentration in saliva, wherein the isolated microorganism is obtained by:
   (a) culturing a microorganism of the genus *Lactobacillus* for 24 h at 37° C. under anaerobic conditions in a synthetic medium containing a starting peptide concentration of 15 g/l of the medium with a starting cell density of $1\times10^7$ cells/ml to obtain a cell culture;
   (b) centrifuging the cell culture at 4000×g for 15 min to obtain a supernatant; and
   (c) determining the peptide concentration of the supernatant and comparing with the starting peptide concentration of the synthetic medium to identify a microorganism which reduces the starting peptide concentration of the synthetic medium by at least 20% after 24 h of incubation.

2. The isolated microorganism of claim 1, wherein the isolated microorganism is further capable of reducing the peptide concentration when in a lyophilized form by:
   (a) culturing the isolated microorganism for 24 h at 37° C. under anaerobic conditions in 100 ml of a synthetic medium with a starting cell density of $1\times10^7$ cells/ml to obtain a cell culture;
   (b) centrifuging the cell culture at 4000×g for 15 min to obtain a first cell pellet, then resuspending the first cell pellet in 20 ml $H_2O$ to obtain a cell suspension;
   (c) freezing the cell suspension to −80° C. and lyophilizing under vacuum for 16 h to obtain lyophilized cells;
   (d) resuspending 10 mg of the lyophilized cells in $H_2O$ and centrifuging at 4000×g for 10 min to obtain a second cell pellet;
   (e) resuspending the second cell pellet in 1 ml of the synthetic medium containing a starting peptide concentration of 7 g/l of the medium and incubating at 37° C. under aerobic conditions for 5 min;
   (f) centrifuging at 4000×g for 15 min to obtain a supernatant; and
   (g) determining the peptide concentration of the supernatant and comparing with the starting peptide concentration of the medium,
   wherein the lyophilized form of the isolated microorganism reduces the starting peptide concentration of the medium by at least 20% after 5 min of incubation.

3. The isolated microorganism of claim 1, wherein the isolated microorganism is further capable of stimulating growth of *Streptococcus salivarius*, but not growth of *Streptococcus mutans* or *Porphyromonas gingivalis*, obtained by:
   (a) culturing the isolated microorganism for 24 h at 37° C. under anaerobic conditions in a synthetic medium and centrifuging the cell culture to obtain a supernatant;
   (b) culturing *Streptococcus salivarius* in a TSY medium, culturing *Streptococcus mutans* in a TSY medium, or culturing *Porphyromonas gingivalis* in a FAB medium;
   (c) mixing the supernatant with *Streptococcus salivarius* in a volumetric ratio of 1:2 to 1:4, mixing the supernatant with *Streptococcus mutans* in a volumetric ratio of 1:2, or mixing the supernatant with *Porphyromonas gingivalis* in a volumetric ratio of 1:2, and culturing under anaerobic conditions; and
   (b) observing growth of *Streptococcus salivarius*, *Streptococcus mutans*, or *Porphyromonas gingivalis*,
   wherein the supernatant stimulates the growth of *Streptococcus salivarius*, but not the growth of *Streptococcus mutans* or *Porphyromonas gingivalis*.

4. The isolated microorganism of claim 1, wherein the isolated microorganism is *Lactobacillus acidophilus*.

5. An inactivated form of the isolated microorganism of claim 1 capable of reducing a starting peptide concentration of 7 g/l of a synthetic medium by at least 20% after 5 min of incubation at 37° C. under aerobic conditions, obtained by:
   (a) culturing the isolated microorganism for 24 h at 37° C. under anaerobic conditions in 100 ml of a synthetic medium with a starting cell density of $1\times10^7$ cells/ml to obtain a cell culture,
   (b) centrifuging the cell culture at 4000×g for 15 min and resuspending in 20 ml $H_2O$ to obtain a cell suspension;
   (c) inactivating the microorganism to obtain an inactivated form of said microorganism;
   (d) centrifuging and resuspending the inactivated form of said microorganism in 1 ml of the synthetic medium containing a starting peptide concentration of 7 g/l of the medium and incubating at 37° C. under aerobic conditions for 5 min;
   (e) centrifuging at 4000×g for 15 min to obtain a supernatant; and
   (f) determining the peptide concentration of the supernatant and comparing with the starting peptide concentration of the medium,
   wherein said inactivated form of said microorganism reduces the starting peptide concentration of 7 g/l of the synthetic medium by at least 20% after 5 min of incubation under aerobic conditions.

6. A composition comprising the inactivated form of the microorganism of claim 5.

7. The composition of claim 6 selected from the group consisting of dentifrices, chewing gums, lozenges, mouth washes, mouth rinses, dental flosses, and dental tapes.

8. A composition comprising the isolated microorganism of claim 1.

9. The composition of claim 8 selected from the group consisting of dentifrices, chewing gums, lozenges, mouth washes, mouth rinses, dental flosses, and dental tapes.

10. An isolated microorganism of the genus *Lactobacillus*, wherein the microorganism stimulates growth of *Streptococcus salivarius*, but does not stimulate growth of *Streptococcus mutans* or *Porphyromonas gingivalis*, obtained by:
    (a) culturing a microorganism of the genus *Lactobacillus* for 24 h at 37° C. under anaerobic conditions in a synthetic medium and centrifuging the cell culture to obtain a supernatant;
    (b) culturing *Streptococcus salivarius* in a TSY medium, culturing *Streptococcus mutans* in a TSY medium, or culturing *Porphyromonas gingivalis* in a FAB medium;
    (c) mixing the supernatant with *Streptococcus salivarius* in a volumetric ratio of 1:2 to 1:4, mixing the supernatant with *Streptococcus mutans* in a volumetric ratio of 1:2, or mixing the supernatant with *Porphyromonas gingivalis* in a volumetric ratio of 1:2, and culturing under anaerobic conditions; and
    (d) observing growth of *Streptococcus salivarius*, *Streptococcus mutans*, or *Porphyromonas gingivalis*,
    wherein the supernatant stimulates the growth of *Streptococcus salivarius*, but not the growth of *Streptococcus mutans* or *Porphyromonas gingivalis*.

11. The isolated microorganism of claim 10, wherein the microorganism is *Lactobacillus acidophilus*.

12. An inactivated form of the isolated microorganism of claim 10 capable of stimulating growth of *Streptococcus sali-*

*varius*, but not growth of *Streptococcus mutans* or *Porphyromonas gingivalis*, by further inactivating the supernatant obtained in step (a) prior to mixing with *Streptococcus salivarius*, *Streptococcus mutans* or *Porphyromonas gingivalis* in step (c) for assaying growth stimulation.

13. A composition comprising the inactivated form of the microorganism of claim 12.

14. The composition of claim 13 selected from the group consisting of dentifrices, chewing gums, lozenges, mouth washes, mouth rinses, dental flosses, and dental tapes.

15. A composition comprising the isolated microorganism of claim 10.

16. The composition of claim 15 selected from the group consisting of dentifrices, chewing gums, lozenges, mouth washes, mouth rinses, dental flosses, and dental tapes.

17. A cell culture supernatant of the microorganism of claim 10.

18. The isolated microorganism of claim 3, wherein the isolated microorganism is *Lactobacillus acidophilus*.

19. The isolated microorganism of claim 3, wherein the microorganism is lyophilized or inactivated.

20. A method for reducing oral malodor and/or halitosis comprising administering
   a) the isolated microorganism of claim 1;
   b) an inactive form of said microorganism; or
   c) a composition comprising said microorganism,
   to a subject suffering from oral malodor and/or halitosis, thereby reducing the amount of oral malodor and/or halitosis produced.

* * * * *

UNITED STATES PATENT AND TRADEMARK OFFICE
CERTIFICATE OF CORRECTION

PATENT NO.        : 8,506,953 B2
APPLICATION NO.   : 12/997035
DATED             : August 13, 2013
INVENTOR(S)       : Mewes Böttner et al.

Page 1 of 1

It is certified that error appears in the above-identified patent and that said Letters Patent is hereby corrected as shown below:

In the Specification:

Column 26, line 46, delete "laponite" and replace it with --LAPONITE® (manufactured by Rockwood Additives Limited)--

Signed and Sealed this
Seventeenth Day of December, 2013

Margaret A. Focarino
*Commissioner for Patents of the United States Patent and Trademark Office*